US012068081B2

(12) United States Patent
Trpkovski et al.

(10) Patent No.: US 12,068,081 B2
(45) Date of Patent: Aug. 20, 2024

(54) HEALTH SERVICE SYSTEM

(71) Applicant: Hawaikiki Telehealth, LLC, Honolulu, HI (US)

(72) Inventors: Tony Trpkovski, Honolulu, HI (US); Paul Trpkovski, Kailua Kona, HI (US)

(73) Assignee: Hawaikiki Telehealth, LLC, Honolulu, HI (US)

( * ) Notice: Subject to any disclaimer, the term of this patent is extended or adjusted under 35 U.S.C. 154(b) by 0 days.

(21) Appl. No.: 17/819,257

(22) Filed: Aug. 11, 2022

(65) Prior Publication Data

US 2023/0070592 A1    Mar. 9, 2023

Related U.S. Application Data

(63) Continuation of application No. 17/524,573, filed on Nov. 11, 2021, now Pat. No. 11,443,856.

(60) Provisional application No. 63/133,411, filed on Jan. 3, 2021.

(51) Int. Cl.
*G16H 80/00* (2018.01)
*G07C 9/00* (2020.01)

(52) U.S. Cl.
CPC ......... *G16H 80/00* (2018.01); *G07C 9/00182* (2013.01); *G07C 9/00904* (2013.01); *G07C 2009/0019* (2013.01)

(58) Field of Classification Search
CPC .............. G16H 80/00; G07C 9/00182; G07C 9/00904; G07C 2009/0019
USPC ................................................ 340/5.7; 705/2
See application file for complete search history.

(56) References Cited

U.S. PATENT DOCUMENTS

| | | | |
|---|---|---|---|
| 6,484,260 B1 | 11/2002 | Scott | |
| 6,581,161 B1 | 6/2003 | Byford | |
| 8,285,560 B2 * | 10/2012 | Gopinathan | G06Q 40/00 600/300 |
| 9,128,471 B1 * | 9/2015 | Shahid | G06Q 30/0267 |
| 9,292,985 B2 * | 3/2016 | Ahearn | G07C 9/00571 |
| 9,418,495 B2 * | 8/2016 | Mackin | G07C 9/215 |
| 9,482,522 B2 | 11/2016 | Motoyama | |
| 9,704,330 B2 * | 7/2017 | Hubner | G07F 9/001 |
| 9,864,842 B2 | 1/2018 | Hyde et al. | |
| 10,229,548 B2 * | 3/2019 | Daniel-Wayman | G07C 9/23 |
| 10,636,527 B2 | 4/2020 | Pulitzer et al. | |

(Continued)

FOREIGN PATENT DOCUMENTS

WO    WO-2020191445 A1 * 10/2020 ............... E05G 1/08
WO    WO-2022093045 A1 *  5/2022

*Primary Examiner* — Nam V Nguyen
(74) *Attorney, Agent, or Firm* — Merchant & Gould P.C.

(57) ABSTRACT

A health service system for caring for the health of a patient. In one example, the health service system operates to present media content in association with a telehealth consultation. The health service system generates a virtual waiting room for display on a patient device, which presents a media content presentation. After the media content presentation has concluded, the health service system facilitates the telehealth consultation between a patient and a care provider. In some configurations the health service system further includes at least one hub care facility. The hub care facility includes a locked door with a scanner that unlocks the locked door upon scanning a time sensitive door unlock code; and a locked medication locker with a scanner that unlocks the locked medication locker upon scanning a medication locker unlock code.

20 Claims, 18 Drawing Sheets

(56) References Cited

U.S. PATENT DOCUMENTS

| | | | |
|---|---|---|---|
| 10,964,418 B2 | 3/2021 | Gershfang et al. | |
| 10,991,190 B1* | 4/2021 | Luthra | G07C 9/27 |
| 11,043,288 B2* | 6/2021 | Gallopyn | G06F 40/174 |
| 11,438,169 B2* | 9/2022 | Mani | H04L 67/52 |
| 2002/0024420 A1* | 2/2002 | Ayala | E05B 5/003 |
| | | | 340/5.61 |
| 2006/0064319 A1* | 3/2006 | Loevner | G16H 40/67 |
| | | | 705/2 |
| 2010/0176919 A1* | 7/2010 | Myers | G07C 9/00857 |
| | | | 340/5.2 |
| 2012/0179479 A1 | 7/2012 | Waterson et al. | |
| 2013/0060576 A1 | 3/2013 | Hamm et al. | |
| 2014/0136238 A1* | 5/2014 | Simon | G16H 10/60 |
| | | | 705/3 |
| 2015/0317860 A1 | 11/2015 | Hubner et al. | |
| 2017/0011179 A1 | 1/2017 | Arshad et al. | |
| 2017/0116384 A1 | 4/2017 | Ghani | |
| 2017/0169635 A1* | 6/2017 | Karlupia | G07C 9/21 |
| 2017/0195322 A1* | 7/2017 | Cho | G07C 9/27 |
| 2018/0033235 A1 | 2/2018 | Dotterweich et al. | |
| 2019/0009956 A1* | 1/2019 | Fitzpatrick | G06F 3/0304 |
| 2020/0342963 A1 | 10/2020 | Mohammad | |
| 2021/0174621 A1* | 6/2021 | Stevenot | G07C 9/00912 |
| 2022/0076812 A1* | 3/2022 | Kamangar | A61B 5/01 |

* cited by examiner

FIG. 17

HEALTH SERVICE SYSTEM

CROSS REFERENCE TO RELATED APPLICATIONS

This application is a continuation of U.S. application Ser. No. 17/524,573, filed Nov. 11, 2021, now U.S. Pat. No. 11,443,856, titled Health Service System, which claims the benefit of U.S. Provisional Application No. 63/133,411, filed Jan. 3, 2021, titled Health Service System, the disclosures of which are hereby incorporated by reference in their entireties.

BACKGROUND

Access to affordable health care is a growing concern around the world. In the United States, healthcare coverage is provided through a combination of private health insurance and public health coverage. However, a significant portion of the population remain uninsured because they cannot afford to pay the high cost associated with private health insurance and/or do not qualify for public health coverage. Even with insurance coverage, the high costs of insurance premiums, deductibles, co-pays and other out-of-pocket expenses make health care services cost prohibitive for millions of people.

SUMMARY

In general terms, the present disclosure relates to a health service system. In one possible configuration and by non-limiting example, the system operates to present media content in association with a health consultation. Various aspects are described in this disclosure, which include, but are not limited to, the following aspects.

One aspect is a method of presenting media content associated with a telehealth consultation. The method includes receiving a request for a telehealth consultation; generating a virtual waiting room for display on the patient device, wherein during the display of the virtual waiting room, the virtual waiting room presents a media content presentation including one or more media content items; determining when the media content presentation has concluded; and facilitating the telehealth consultation between a patient and a care provider after the media content presentation has concluded.

Another aspect is a system for presenting media content associated with a telehealth consultation. The system includes a processing unit; and system memory, the system memory including instructions which, when executed by the processing unit, cause the system to receive a request for a telehealth consultation; generate a virtual waiting room for display on the patient device, wherein during the display of the virtual waiting room, the virtual waiting room presents a media content presentation including one or more media content items; determine when the media content presentation has concluded; and facilitate the telehealth consultation between the patient and the care provider after the media content presentation has concluded.

Yet another aspect is a healthcare system. The healthcare system includes at least one hub care facility, wherein each of the at least one hub care facilities include: a locked door with a scanner that unlocks the locked door upon scanning a time sensitive door unlock code; a locked medication locker with a scanner that unlocks the locked medication locker upon scanning a medication locker unlock code; a processing unit; and system memory, the system memory including instructions which, when executed by the processing unit, cause a system for presenting media content associated with a health consultation to: receive a request for a telehealth consultation; generate a virtual waiting room for display on a patient device, wherein during the display of the virtual waiting room, the virtual waiting room presents a media content presentation including one or more media content items; determine when the media content presentation has concluded; facilitate the telehealth consultation between the patient and the care provider after the media content presentation has concluded; receive a request device to schedule an appointment for the patient at a hub care facility; and upon receiving a request to schedule the appointment at the hub care facility, send a time sensitive door unlock code to the patient device.

BRIEF DESCRIPTION OF DRAWINGS

FIG. 17 illustrates another example user interface of the provider service of the health care provider system of FIG. 1, as displayed on a telehealth care provider computing device.

DETAILED DESCRIPTION

Figure 1:
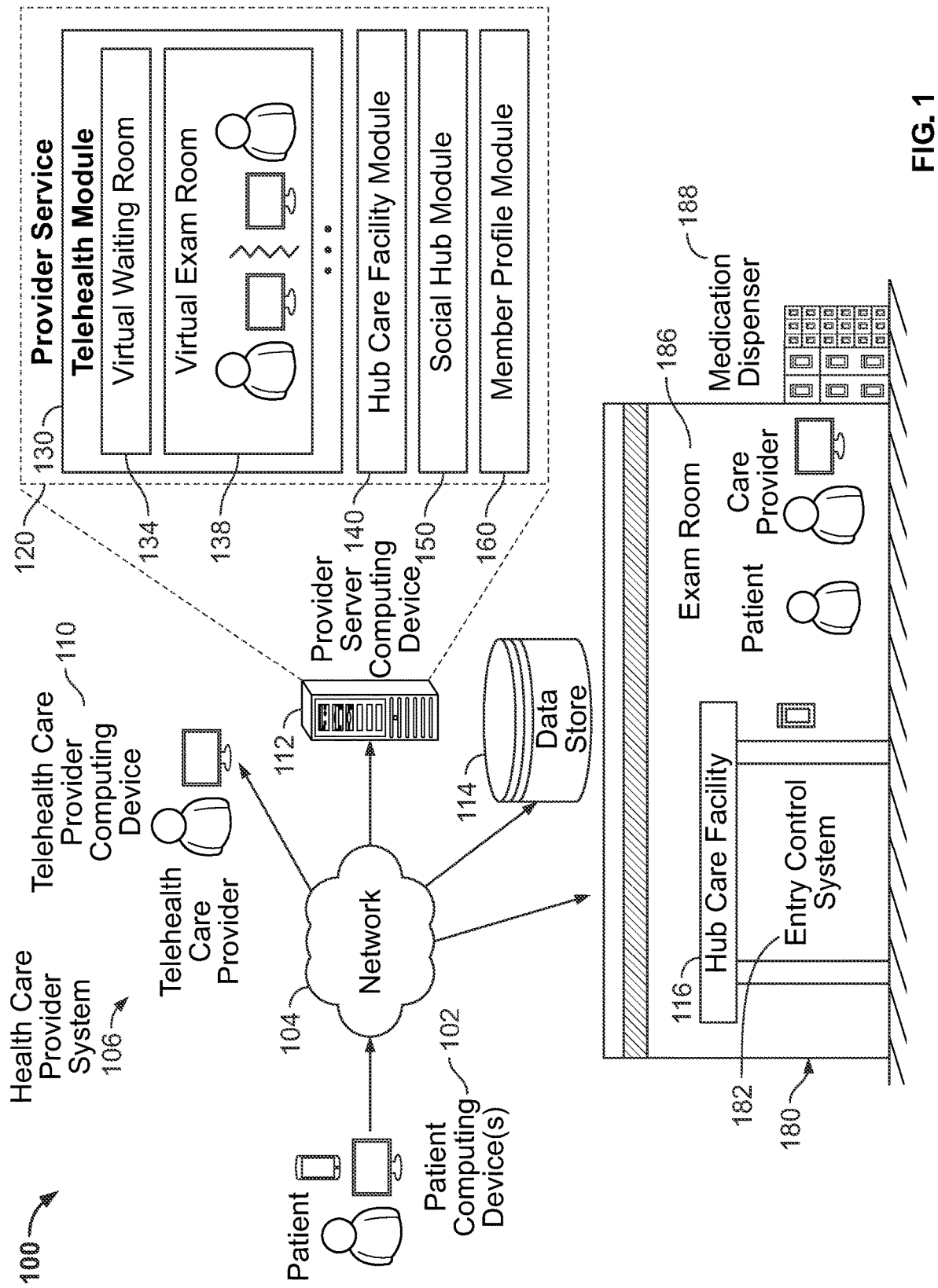
FIG. 1 illustrates an example health service system, including a health care provider system.

Various embodiments will be described in detail with reference to the drawings, wherein like reference numerals represent like parts and assemblies throughout the several views.

In general, the present disclosure provides a health service system that facilitates health services at a reduced cost for the patient by presenting one or more media content items associated with the health consultation to the patient before the health consultation. For example, the disclosed health services include telehealth consultation services and in-person consultation services in one of a plurality of hub care facilities that form the health service system.

Telehealth consultation services include the user of electronic information and telecommunication technologies to support remote clinical health care, patient and care provider health-related education and public health administration services among other health related services. Telehealth consultation services may be facilitated by using videoconferencing, streaming media, and wireless communication over the internet. Other methods of implementing telehealth consultation services is also possible.

In the present disclosure, prior to the initiation of a telehealth consultation, the patient may be exposed to the playback of a media content presentation. In some examples, the media content presentation may include one or more media content items that are directed to the patient's areas of interest. For example, data related to the patient may be used by the disclosed health services system to select media content items that are of particular interest to the patient. In one example, the selected media content items may include directed media content such as advertisements. In some examples, the revenue generated from facilitating the playback of the one or more media content items may be used to offset the cost of health care for the patient.

Although the following disclosure is described in relation to the health care services, the disclosed system related to presenting media content in association with a service may be implemented in other industries such as veterinary health services, transportation services, or any other service that requires payment from customers.

FIG. 1 illustrates an example health service system 100 for providing health services to patients. In some embodiments, health service system 100 includes one or more patient computing device(s) 102 that are in communicative connection with a health care provider system 106 through a network 104.

In some examples, the one or more patient computing device(s) 102 may include electronic computing devices such as a laptop computer, desktop computer, a mobile device such as a smart phone or tablet device, or any type of electronic device that supports the execution of one or more applications related to the health care provider system 106. The one or more patient computing device(s) 102 may be operated by a patient or another user associated with the patient to consult with a care provider regarding a health condition.

The example network 104 may be a computing device network that may include the Internet, private networks, and a combination thereof. In some arrangements, the network 104 includes wired and/or wireless networks. As noted, in this example, the one or more patient computing device(s) 102 can communicate with the devices in the health care provider system 106 using the network 104.

In some examples, the health care provider system 106 includes one or more computing devices, including a telehealth care provider computing device 110, a provider server computing device 112, one or more data stores 114 and a hub care facility 116, which may include one or more associated computing devices. The one or more patient computing device(s) 102 may be communicatively connected to the one or more computing devices included within the health care provider system 106 through the network 104.

In some examples, the telehealth care provider computing device 110 may include electronic computing devices such as a laptop computer, desktop computer, a mobile device such as a smart phone or tablet device, or any type of electronic device that supports the execution of one or more applications related to the health care provider system 106. The telehealth care provider computing device 110 may be operated by a telehealth care provider or another user associated with the telehealth care provider to consult with a patient regarding a health condition.

In the example provider server computing device 112 is a server computer that can include the provider service 120. In some examples, the provider server computing device 112 may be a server computer of a health care provider. In other examples, the provider server computing device 112 may be a server computer associated with a different enterprise. Although a single server computer 112 is shown in the health care provider system 106, in reality, the provider server computing device 112 can be implemented with multiple computing devices, such as a server farm or through cloud computing. Many other configurations are possible.

In some examples, the provider service 120 is implemented in example provider server computing device 112. For example, the provider service 120 is configured to receive patient and care provider requests and facilitate a health consultation between the patient and the care provider. The example provider service 120 can include a computer implement application with functionality or set of functionalities that the plurality of patients and care providers can request and use for different purposes. For example, the provider service 120 may be an application that includes a patient portal and a care provider portal that offer different functionality based on if the user is the patient or the care provider. In most cases, the care provider portal may include some supplementary functionality in addition to all the functionalities available to the patient.

In some examples, the provider service 120 includes a telehealth module 130, a hub care facility module 140, a social hub module 150, and a member profile module 160. In other examples, the provider service 120 may be configured to include more or less number of modules or the functionality of the modules 130, 140, 150 and 160 may be configured differently.

The example telehealth module 130 is configured to facilitate a telehealth consultation between a patient and a telehealth care provider following a presentation of one or more media content items. For example, the telehealth module 130 may include a virtual waiting room 134 and a virtual exam room 138 among other sub-modules. The virtual waiting room 134 and virtual exam room 138 are user interface displays generated by the provider service 120 and sent to the patient computing device 102 or the telehealth care provider computing device 110 for display on a display screen.

In some examples, upon requesting a telehealth consultation, the patient computing device 102 may display a virtual waiting room user interface generated by the virtual waiting room 134 where the patient may be presented with a presentation with one or more media content items that the patient views prior to being placed in a queue for the telehealth consultation. After being placed in the queue, the patient computing device 102 may continue to display the virtual waiting room user interface generated by the virtual waiting room 134 until the telehealth care provider is ready. When the telehealth care provider becomes available, the patient may be moved to a virtual exam room user interface generated by the virtual exam room 138 where the telehealth care provider may begin the consultation with the patient. The configuration and functionality of the telehealth module 130 is described in further detail in association with FIG. 2.

In some examples the hub care facility module 140 is configured to facilitate an in-person health consultation between the patient and a care provide. In other examples, the hub care facility is configured to facilitate medication pickup for a patient. For example, following a telehealth consultation with a patient, a telehealth provider may determine that the patient's health condition necessitates an in-person visit at a hub care facility 116 or medication that can be picked up from a hub care facility 116. The telehealth care provider and the patient may use the hub care facility module 140 of the provider service 120 to facilitate the in-person health consultation and/or medication pickup. The hub care facility module 140 is described in greater detail in association with FIG. 3.

The example social hub module 150 is configured to include one or more "community" pages associated with health conditions or lifestyle that the patient can read or browse. The social hub module 150 may also be configured to include a marketplace where the patient may purchase products and services associated with healthy living. The example member profile module 160 is configured to manage authentication of the patient, account settings data, biographical/demographical data related to the patient, electronic medical records associated with the patient and payment information associated with the patient. The member profile module 160 may be configured to include other features and functionality. The example social hub module 150 and member profile module 160 are described in further detail in relation to FIGS. 4-5.

The example data store 114 may include one or more electronic databases that can store patient data, care provider data, media content data, etc. Other types of data may also be stored in the one or more data stores. The one or more data stores 114 can be accessed by the provider service 120 to store and retrieve relevant data. In some examples, the provider server computing device 112 may be communicatively connected to the one or more data stores 114. In other examples, the one or more data stores 114 may be included within the provider server computing device 112. In another example, the one or more data stores 114 may be maintained by the same enterprise that maintains the provider server computing device 112 and in yet another example, the one or more data stores 114 may be maintained by an external third-party enterprise. Other configurations are also possible.

In some examples, when a telehealth care provider deems it necessary for the patient to consult with a care provider in person or otherwise visit a care facility in person for medication pick-up or lab work, the telehealth provider may refer the patient a hub care facility 116. The example hub care facility 116 includes a building 180 that houses the hub care facility 116. The building 180 may include an entry control system 182 that controls entry to the building 180 through locked doors that can be unlocked by providing an unlock code. The building 180 may also house one or more exam rooms 186 where a care provider may consult with the patient in-person. In some examples, the building 180 may include a medication dispenser 188 that includes a plurality of locked medication lockers that may be stocked with the patient's medication. The patient may unlock the appropriate medication locker using an unlock code to retrieve the patient's medications. The hub care facility 116 is described in detail in relation to FIG. 4.

Figure 2:
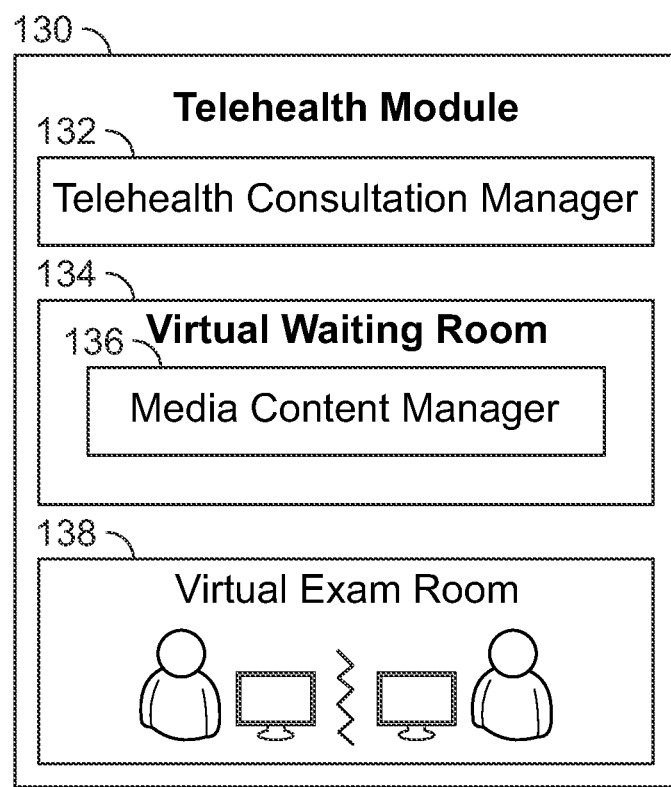
FIG. 2 illustrates an example configuration of a telehealth module of the provider service of the health care provider system of FIG. 1.

FIG. 2 illustrates an example configuration of the telehealth module 130. The example telehealth module 130 facilitates a remote health consultation between a patient and a telehealth care provider upon determining that the patient has viewed a media content presentation. In some examples, the telehealth module 130 includes a telehealth consultation manager 132, a virtual waiting room 134, a media content manager 136 and a virtual exam room 138.

In some examples, the telehealth consultation manager 132 manages the initial patient request to consult with a telehealth care provider. The example telehealth consultation manager 132 receives data associated with the patient and initiates the telehealth consultation. In some examples, the patient, using a patient portal of the provider service 120 on a patient computing device 102, initiates a telehealth visit. The telehealth consultation manager 132 manages the initiation or "check-in" process of the telehealth visit by requesting the patient to provide information regarding the current reason for the visit. The telehealth consultation manager 132 may also request the patient to select a telehealth care provider from a plurality of telehealth care providers. Upon receiving the requested information, the telehealth consultation manager 132 stores the data in data store 114. The stored data may be used as part by the media content manager 136 or other modules of the provider service 120.

In some examples, after completing the "check-in" process, the virtual waiting room 134 generates a virtual waiting room user interface to be displayed on the patient computing device 102. The example virtual waiting room 134 may include a media content manager 136 that may cause the playback of a media content presentation on the patient computing device 102 while the virtual waiting room 134 causes the display of the virtual waiting room user interface on the patient computing device 102. In some examples, the media content presentation may include one or more media content items. The example media content items may include directed content such as advertisements, or other informational media content items related to the care provider and/or the patient's health condition.

In some examples, the virtual waiting room user interface remains displayed on the patient computing device 102 until the playback of the media content presentation is completed.

In other examples, the options on the virtual waiting room user interface may prevent the facilitation of the telehealth consultation until the media content presentation has concluded by locking out or otherwise disabling any selections on the waiting room user interface until playback of the media content presentation has concluded. In some examples, the telehealth care provider that will be providing care to the patient may have an option to disable the lock and interrupt the playback of the media content presentation in order to commence the telehealth consultation before the playback of the media content presentation has concluded.

For example, the virtual waiting room 134 may generate a virtual waiting room user interface to be displayed on the patient computing device 102 and automatically begin playback of the media content media content presentation on the virtual waiting room user interface to be displayed on the patient computing device 102. In other cases, the playback need not be automatic and can be triggered upon the user selecting an option to begin playback of the media content presentation.

During the playback of the media content presentation, the virtual waiting room 134 may cause an initiation of a lockout mode on the virtual waiting room user interface. In some examples, a lock out mode may include preventing the patient from being able to make any selections on the virtual waiting room user interface until the media content presentation has concluded. In other examples, a lock out mode may include allowing the patient to still make some selection, such as a selection to exit the media content presentation, but preventing the patient from making other selections, such as any selections that would initiate the telehealth consultation until the media content presentation has concluded.

In some examples, the media content manager 136 may be configured to select one or more media content items to be included in the media content presentation. In some examples, the media content presentation is for a predetermined amount of time, such as 5 minutes. In other examples, the media content presentation may include a predetermined number of media content items, such as 3 advertisements.

The length of the media content presentation may be based on the type of appointment. For example, the length of the media content presentation may be directly proportional to the estimated length of the consultation. In one example, for a telehealth consultation involving typical health conditions such as cold like symptoms, headaches, pinkeye, etc., the length of the media content presentation may be relatively short. For other types of telehealth consultations, such as a therapy session that may last longer than a typical telehealth visit, the length of the media content presentation may be longer, such as 15 minutes. Other factors may also impact the length of media content presentation.

In some examples, the media content manager 136 may select one or more media content items based on data associated with the patient. For example, patient related data, including biographical/demographical data, health history data and other data from the patient's electronic medical records, patient's browsing history and purchase history related to the social hub module 150 and the patient's current symptoms and reason for visit as collected and stored by the telehealth consultation manager 132 can be retrieved from the one or more data stores 114. The retrieved data may be analyzed using a data model that predicts the patient's areas of interests and selects one or more media content items for the media content presentation that aligns with the patient's interests.

For example, if a particular patient's electronic medical records indicate that the patient is diabetic, and the patient's browsing history on the social hub indicates that the patient was browsing articles regarding lifestyle changes that would help treat diabetes, then the media content presentation may include an advertisement for a particular brand of blood glucose test strips or an advertisement for running shoes that encourage patients to exercise may be selected for the media content presentation that is presented to that particular patient.

By selecting media content items for the media content presentation that are highly relevant to the patient, the health care provider system 106 may be able to generate revenue from the creators or owners of the media content items. The revenue generated from presenting one or more media content items to the patient can be used to offset the cost of health care for the patient.

In some examples, the media content presentation may include one or more media content items that are interactive and requires input from the patient to ensure that the patient is focused on the media content presentation. Other ways of ensuring that the patient is focused on the media content presentation is by using sensors and analysis software, including cameras and movement sensors to analyze the patient's facial features and eye movement to ensure that the patient is viewing the media content presentation. In other examples, the media content manager 136 may receive periodic data from one or more sensors, including cameras and movement sensors, associated with the patient computing device 102 regarding the patient's facial features, such as eye movements, to ensure that the patient remains focused on the media content presentation during the entire length of the playback of the media content presentation.

In some examples, the virtual waiting room 134 determines that the media content presentation has concluded based on the completion of the playback of the media content presentation. In other examples, if the patient does not want to view the media content presentation before consulting with the telehealth care provider, then the patient may be able to pay a fee to skip the media content presentation.

Upon determining that the media content presentation has concluded or that the patient has paid a fee to skip the media content presentation altogether, the patient may be placed in a virtual queue until the telehealth care provider is available to consult with the patient. The patient computing device 102 may receive a message indicating that the patient has been placed in a queue. In some examples, the message may also include an estimated time until the consultation.

Concurrently, the telehealth care provider computing device 110 may receive a message indicating that a patient has completed the playback of the media content presentation and is in a queue waiting for their telehealth consultation.

In some examples, when the telehealth care provider is ready to consult with the patient, the telehealth care provider may select to start the telehealth consultation with the patient and the patient and the user interface of the provider service 120 on both the patient computing device 102 and the telehealth care provider computing device 110 may update to display the virtual exam room user interface generated by the virtual exam room 138 of the telehealth module 130.

In some examples, the virtual exam room 138 may be configured to facilitate a telehealth consultation between a patient and a telehealth care provider. For example, the virtual exam room 138 may be configured to enable a camera and microphone associated with the patient computing device 102 and the telehealth care provider computing device 110 in order to enable better communication between the patient and the telehealth care provider.

In some examples, based on the telehealth care provider's consultation with the patient, the telehealth care provider may take one of several actions. For example, the telehealth care provider may advise the patient to take over the counter medication, go to a hospital or a specialist clinic or take no action. In other examples, the telehealth care provider may advise the patient to take further action including visiting a hub care facility for further in-person consultation with a care provider, lab testing or to pick up prescription medications. Service associated with the patient visiting a hub care facility 116, such as in-patient consultation, lab work, medication pickup, are described in further detail in relation to FIG. 3.

Figure 3:
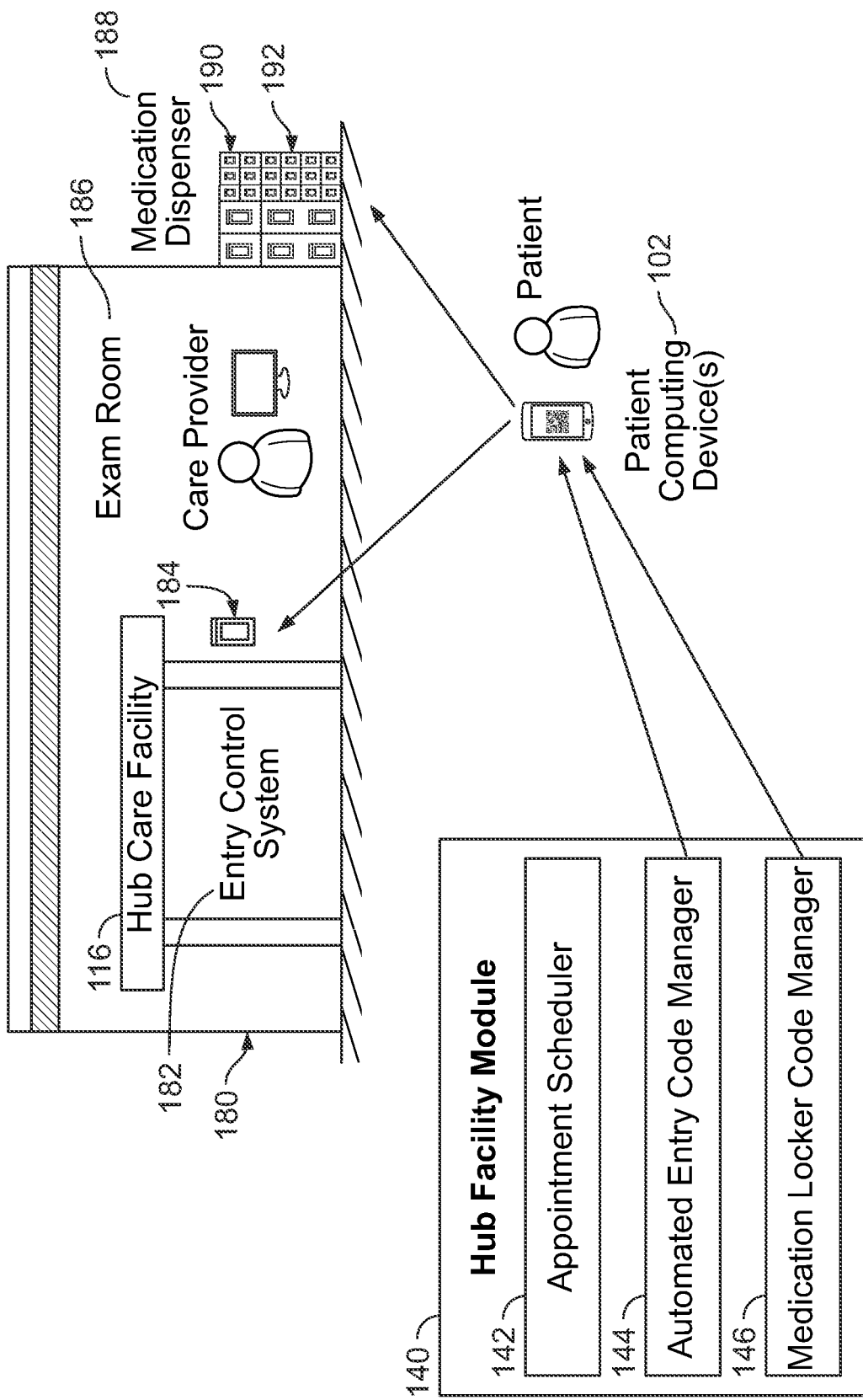
FIG. 3 illustrates an example configuration of the hub facility module of the provider service of the health care provider system of FIG. 1.

FIG. 3 illustrates an example configuration of the hub facility module 140. The hub facility module 140 of the provider service 120 is configured to communicatively connect with the computing devices of the hub care facility 116 and facilitate in-person care consultations, medication pick-ups and lab testing following a telehealth consultation. The hub facility module 140 includes an appointment scheduler 142, and automated entry code manager 144 and a medication locker code manager 146.

In some examples, the hub care facility 116 includes a building 180 that houses one or more computing devices that communicatively connects to the hub facility module 140. For example, the building 180 includes an entry control system 182 that includes a door lock scanner 184 that controls entry into the building 180 and a medication dispenser 188 that includes one or more medication lockers 190 that each include a medication locker scanner 192 that control access to the medication locker. The building 180 also includes one or more exam rooms 186 where a care provider may use the provider services 120 through a care provider computing device to facilitate in-person consultations with patients.

In some examples, the appointment scheduler 142 is configured to facilitate the scheduling of appointments for in-person consultations between patients and care providers. In some examples, following a telehealth consultation using the telehealth module 130 (described above in relation to FIG. 2), if the telehealth care provider deems that the patient would benefit from an in-person consultation, then the telehealth provider may schedule an appointment for the patient to visit a hub care facility 116 of the patient's choice at a date and time that is convenient for the patient using an appointment scheduler 142 on the hub facility module 140. In other examples, the telehealth care provider may approve of an in-person consultation and the patient may schedule an appointment for an in-person consultation at their convenience using the appointment scheduler 142. In some examples, the patient may not be able to schedule an in-person appointment without the approval of the telehealth care provider. In other examples, the patient schedule in-person appointments without first consulting with the telehealth care provider.

In some examples, the automated entry code manager 144 is configured to provide the patient with an unlock code that unlocks the entry control system of the hub care facility 116 when the unlock code is entered into the door lock scanner 184. For example, after an in-person appointment for a consultation or lab work is scheduled by the telehealth care provider or the patient using the appointment scheduler 142, the automated entry code manager 144 generates and sends a door unlock code to the patient computing device 102.

In some examples, the door unlock code may be a Quick Response code (QR code) or a bar code. In other examples, the door unlock code may be a numerical code or alphanumerical code. In some examples, the door unlock code may be time sensitive such that the unlock code is only valid for a predetermined duration surrounding the scheduled appointment date and time. For example, the door unlock code may only be valid 15 minutes prior to the appointment time and the door unlock code may become invalid 30 minutes after the start of the appointment time. The automated entry control system 182 helps minimize the operating cost of the hub care facility 116.

In some examples, the door unlock code may be received by the patient along with an appointment confirmation message. The patient may then be able to print the door unlock code or in case of a mobile device, bring the mobile device to the hub care facility where the door unlock code may be scanned using the door lock scanner 184 to unlock the entry control system and gain entry into the building 180. In other examples, where the door unlock code is a numerical code, the patient may enter the code on the door lock scanner 184 to gain access to the building 180.

In some examples, the medication locker code manager 146 may be configured to facilitate medication pick-up using the medication dispenser 188. For example, after a telehealth care provider or an in-person care provider prescribes one or more medication to a patient, the patient may have the option to use hub facility module to pay for the medication and schedule a medication pick-up date and time. Once the medication pick-up date and time are scheduled, the prescribed medication may be stocked by a staff member or an automated mechanical process within a particular medication locker 190. The patient computing device 102 may then receive a message with a confirmation message with the scheduled pick-up date and time and a medication locker number and medication locker unlock code generated by the medication locker code manager 146 to unlock the medication locker 190 that corresponds to the medication locker number.

Similar to the door unlock code, the medication locker unlock code may be a time sensitive code that is only valid within a predetermined duration surrounding the scheduled pick-up time. The medication locker unlock code may be a QR code, bar code, numerical code or an alpha numerical code that the patient or patient's representative may use in association with the medication locker scanner 192 associated with the medication locker 190 with the medication locker number listed on the confirmation message to unlock medication locker 190 and retrieve the prescribed medication.

Figure 4:
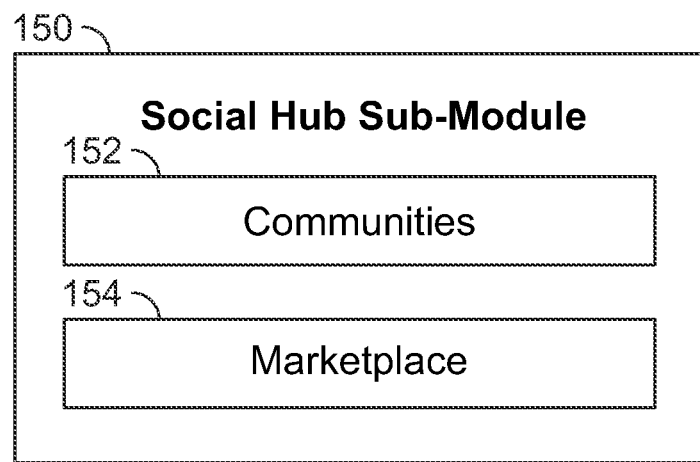
FIG. 4 illustrates an example configuration of the social hub module of the provider service of the health care provider system of FIG. 1.

FIG. 4 illustrates an example configuration of the social hub module 150. The example social hub module 150 may be configured to be a social resource for patients and may include a communities sub-module 152 and a marketplace 154. The communities sub-module 152 serves as a resource for the patient and includes one or more "community" pages, blog entries, articles, videos and other related to health, wellness and lifestyle.

For example, a community page may be a virtual group associated with a topic related to health, wellness or lifestyle that patients can join to connect with other users with similar interests. A community page may include articles and message boards where group members may discuss ideas and share resources associated with the topic. In one example, the communities sub-module may include a community page related to running that patients interested in running can join or a heart disease page that patients with heart conditions can join.

In some examples, the communities sub-module 152 may also include a blog maintained by the provider to discuss topics that are of interest to the health practice and patients. In other examples, the communities sub-module 152 may also include health, wellness and lifestyle related articles, videos, frequently asked questions page, etc.

In some examples, the social hub module 150 may be configured to include a marketplace 154 where the patient may purchase products and services associated with healthy living. For example, the marketplace 154 may include a plurality of health, wellness and lifestyle related products and services such as vitamins, supplements, exercise equipment, running shoes, kitchen tools, fitness trackers, etc. Other types of products and services may also be sold through the marketplace 154.

Figure 5:
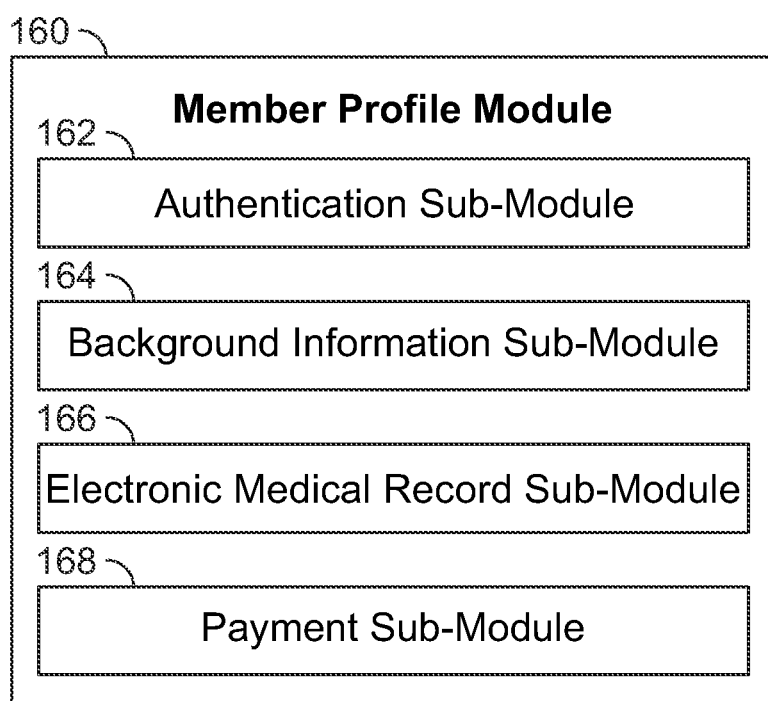
FIG. 5 illustrates an example configuration of the member profile module of the provider service of the health care provider system of FIG. 1

FIG. 5 illustrates an example configuration of the member profile module 160. The example member profile module 160 is configured to manage data related to the patient. For example, the member profile module 160 includes an authentication sub-module 162, a background information sub-module 164, an electronic medical record sub-module 166 and a payment sub-module 168. The member profile module 160 may also be configured to include other features and functionality related to the patient.

In one example, the authentication sub-module 162 may be configured to authenticate the patient and the care providers. For example, the authentication sub-module may receive authentication credentials from a patient and compare the received information to authentication data stored in the data store 114 to authenticate the user. In some examples, the authentication data may include a username and a password. Other types of authentication data are also possible.

In some examples, the background information sub-module 164 may be configured to manage background information related to the patient including biographical and demographical information such as name, age, height, weight, race, ethnicity, sex, family members, etc. In other examples, the background information related to the patient may include address, insurance information, employment information, contact information, income information, consent forms, emergency contacts and other patient account related information.

In some examples, the patient account information may include the patient's plan selections. For example, the health care provider system 106 may be operated as a monthly or yearly subscription service. The patient may be able to select a subscription plan based on the patient's needs.

The background information sub-module may be configured to store the background information in the one or more data stores 114 and to access the stored background information when requested.

In some examples, the electronic medical record sub-module 166 may be configured to manage the electronic medical records associated with the patient. For example, the electronic medical records associated with the patient may include health history data, care provider notes associated with each visit, medication information, allergy information, etc. In some examples, the patient may be able to add notes to the electronic medical record as well.

In some examples, the payment sub-module 168 may be configured to manage the payment information related the patient. The example payment sub-module may store credit/debit card information and/or bank account information related to the patient in one or more data stores 114 that may be accessed by the payment sub-module 168. For example, the payment sub-module may use the payment data to pay for the account subscription payments, medication payments, and payments for any products or services purchased through the marketplace 154.

Figure 6:
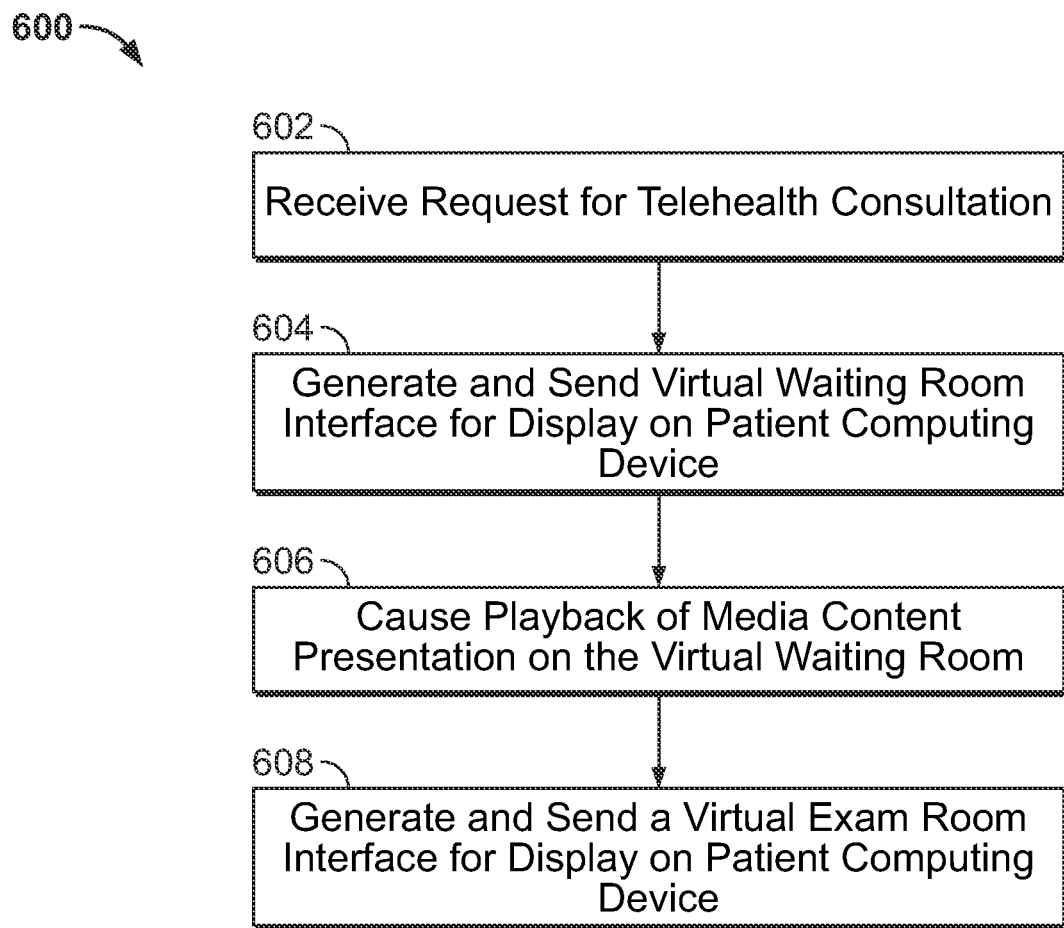
FIG. 6 illustrates an example method for operating the telehealth module of FIG. 2.

FIG. 6 illustrates an example method 600 for operating the telehealth module 130 of the provider service 120. In some examples, the method 600 may be performed by the provider server computing device 112. In other examples, the method 600 can be performed by another one or more other computing devices.

At operation 602, the telehealth module 130 of the provider service 120 receives a request for a telehealth consultation from a patient computing device 102. The request for the telehealth consultation may include a brief summary of the reason for the request and a selection of a telehealth care provider. In some examples, the request for a telehealth consultation is submitted close to the time when the patient prefers to conduct the consultation. However, in other examples, a method for scheduling a time for a future telehealth consultation is also possible. Upon receiving the request for a telehealth consultation, the telehealth consultation manager 132 processes the request and initiates operation of 604.

At operation 604, the virtual waiting room 134 of the telehealth module 130 generates and sends a virtual waiting room interface for display on the patient computing device 102. In some examples, the virtual waiting room interface is displayed on the patient computing device 102 and the patient is asked to view the media content presentation as described in operation 606 before the patient can be placed on a virtual queue to consult with the telehealth care provider.

At operation 606, the media content manager 136 of the telehealth module 130 causes the playback of a media content presentation on the virtual waiting room interface. In some examples, the virtual waiting room interface may include a portion of the display where a media content presentation may be displayed for the patient to view. In some examples, the media content manager 136 may analyze patient related data and generate a media content presentation with one or more media content items that are directed at the patient's interests. The virtual waiting room 134 may cause the playback of the generated media content presentation on the virtual waiting room interface that is displayed on the patient computing device 102.

In some examples, upon determining that the playback of the media content presentation has concluded, the patient is placed in a virtual queue until the telehealth care provider is available for the consultation. The patient computing device 102 continues to display the virtual waiting room interface until the telehealth provider initiates the telehealth visit and the user interface is changed to the virtual exam room interface in operation 608.

At operation 608, upon determining that the telehealth care provider has initiated the telehealth visit, the virtual exam room 138 of the telehealth module 130 generates and send a virtual exam room interface for display on patient computing device. In some examples, the virtual exam room 138 may send a prompt to the patient computing device 102 and the telehealth care provider computing device 110 to enable a camera and/or microphone to facilitate the telehealth consultation.

In some examples, upon concluding the telehealth consultation with the patient, the telehealth care provider may not require any further actions from the patient. In other examples, the telehealth care provider may recommend that the patient schedule an in-person consultation with a care provider at a hub care facility 116, pick up prescribed medication from a medication dispenser 188 at the hub care facility 116 or schedule an appointment for an in-person visit to the hub care facility 116 to get lab work done. The method of operation associated with the hub care facility module to schedule an in-person visit to a hub care facility 116 is described in further detail in relation to FIG. 7.

Figure 7:
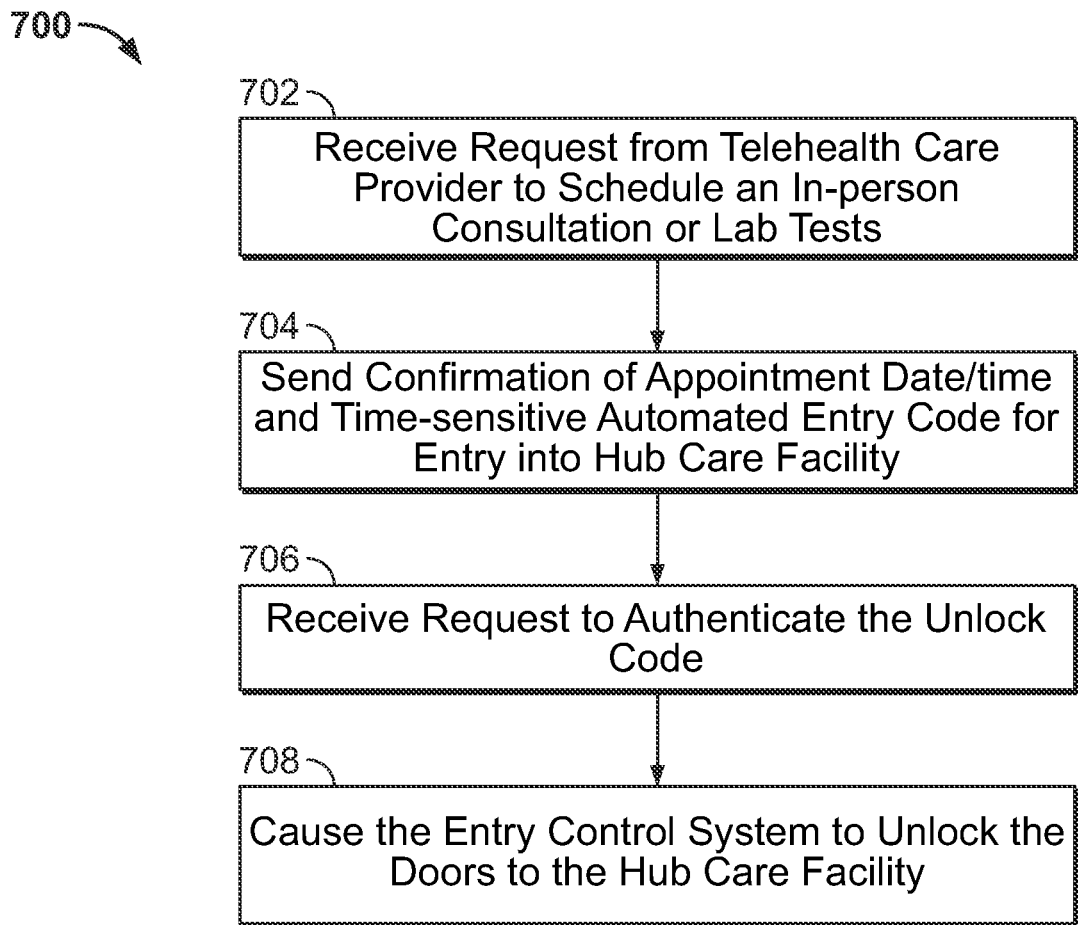
FIG. 7 illustrates an example method for operating the hub care facility module of FIG. 3.

FIG. 7 illustrates an example method 700 for operating the hub care facility module 140 of the provider service 120. In some examples, the method 700 may be performed by the provider server computing device 112. In other examples, the method 600 can be performed by another one or more other computing devices. In some examples, a similar process to operations 702-708 may be performed when a request for medication pickup is received by the hub care facility module 140.

At operation 702, the appointment scheduler 142 receives a request from a telehealth care provider computing device 110 to schedule an in-person consultation or lab testing within the hub care facility building 180. In some examples, the patient may schedule the consultation or lab testing visit to the hub care facility upon receiving approval from the telehealth care provider. In other examples, the telehealth care provide may schedule the visit at the conclusion of the telehealth consultation. For example, the telehealth care provider may request the patient to provide a date, time and the most convenient location of the hub care facility 116 among a plurality of hub care facilities. Based on the information provided by the patient, the telehealth care provider may schedule the appointment for the visit.

At operation 704, appointment scheduler 142 and the automated entry code manager 144 send one or more messages to the patient computing device 102 confirming the date and time of the scheduled in-person visit and including a time-sensitive automated entry code for entry into the hub care facility building 180. In some examples, upon receiving a request to schedule an appointment, the automated entry code manager 144 may automatically generate a time sensitive door unlock code to unlock the entry control system 182 associated with the selected hub care facility location within a time window surrounding the selected appointment date and time. The patient may then present the received door unlock code at the entry control system 182 using the door lock scanner 184 during the designated time to gain access to the selected hub care facility building 180.

At operation 706, the automated entry code manager 144 receives a request from the entry control system 182 to authenticate the unlock code provided by a patient through the door lock scanner 184. For example, upon receiving the door unlock code at the patient computing device 102, the patient may enter the door unlock code through the door lock scanner 184 to gain access to the hub care facility building 180. Upon the patient entering the door unlock code on the door lock scanner 184, the automated entry control system 182 sends and the automated entry code manager 144 of the hub care facility module 140 receives the entered door unlock code.

At operation 708 the automated entry code manager 144, upon authenticating the received door unlock code, causes the entry control system 182 to unlock the doors to the hub care facility building 180. In some examples, the unlock code may be generated to be unique to the patient and using the authentication code to gain entry to the hub care facility building 180 may also serve to check-in the patient at the hub care facility 116.

Figure 8:
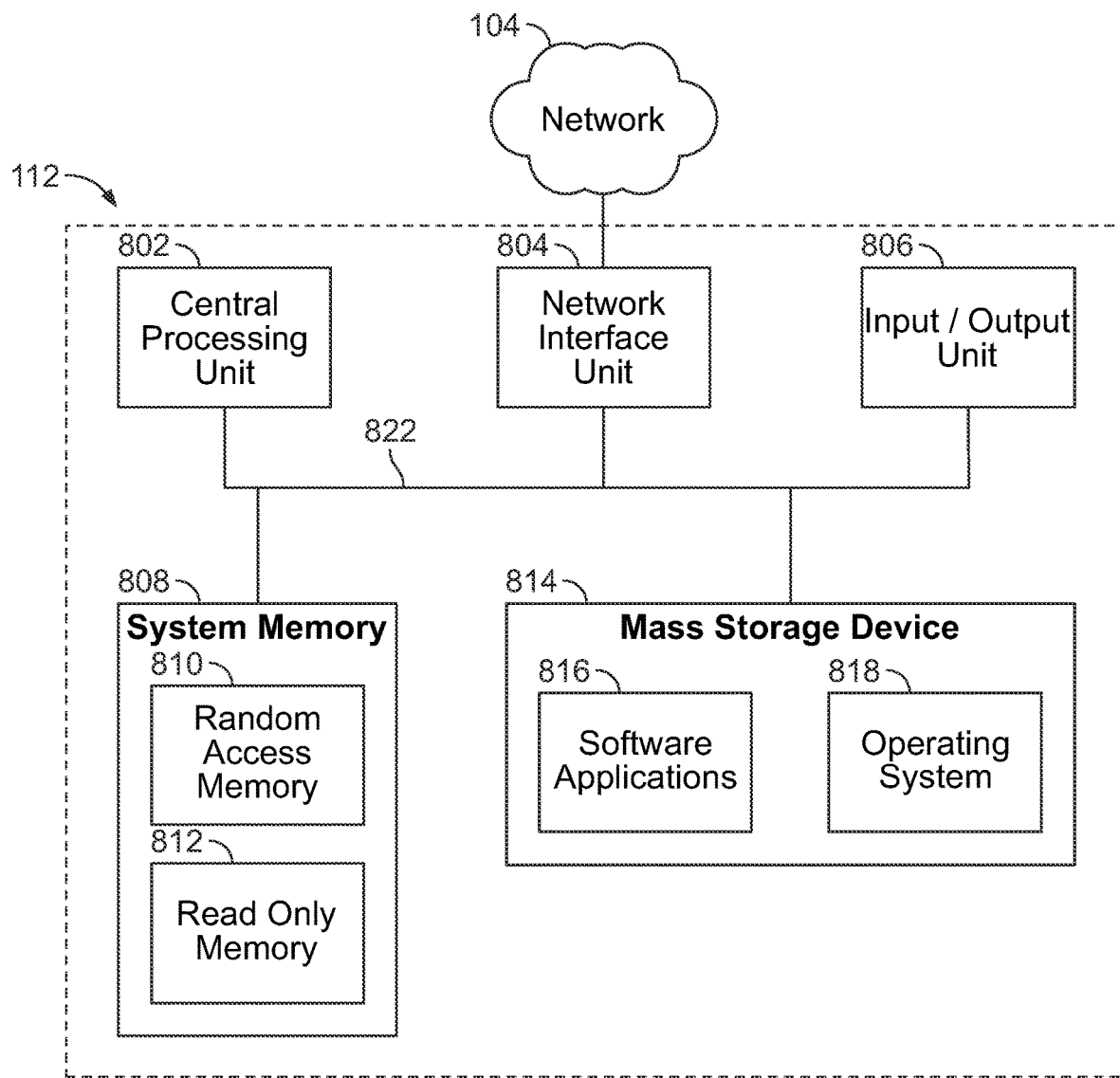
FIG. 8 illustrates example physical components of the provider server computing device of the health care provider system of FIG. 1.

FIG. 8 illustrates example physical components of the provider server computing device 112 of the health care provider system 106 of FIG. 1. As illustrated in the example of FIG. 8, server computer 112 includes at least one central processing unit ("CPU") 802, a system memory 808, and a system bus 822 that couples the system memory 808 to the CPU 802. The system memory 808 includes a random-access memory ("RAM") 810 and a read-only memory ("ROM") 812. A basic input/output system that contains the basic routines that help to transfer information between elements within the server computer 112, such as during startup, is stored in the ROM 812. The provider server computing device 112 further includes a mass storage device 814. The mass storage device 814 is able to store software instructions and data, including software applications 816, including the provider service 120 and an operating system 818.

The mass storage device 814 is connected to the CPU 802 through a mass storage controller (not shown) connected to the system bus 822. The mass storage device 814 and its associated computer-readable data storage media provide non-volatile, non-transitory storage for the provider server computing device 112. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the central processing unit can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the provider server computing device 112.

According to various embodiments of the invention, the provider server computing device 112 may operate in a networked environment using logical connections to remote network devices through the network 104, such as a wireless network, the Internet, or another type of network. The provider server computing device 112 may connect to the network 104 through a network interface unit 804 connected to the system bus 822. It should be appreciated that the network interface unit 804 may also be utilized to connect to other types of networks and remote computing systems. The provider server computing device 112 also includes an input/output controller 806 for receiving and processing input from a number of other devices, including a touch user interface screen, or another type of input device. Similarly, the input/output controller 806 may provide output to a touch user interface screen or other type of output device.

As mentioned briefly above, the mass storage device 814 and the RAM 810 of the provider server computing device 112 can store software instructions and data. The software instructions include one or more software applications 816. The software instructions can also include an operating system 818 suitable for controlling the operation of the provider server computing device 112. The mass storage device 814 and/or the RAM 810 also store software instructions, that when executed by the CPU 802, cause the provider server computing device 112 to provide the functionality of the provider server computing device 112 discussed in this document. For example, the mass storage device 814 and/or the RAM 810 can store software instructions that, when executed by the CPU 802, cause the provider server computing device 112 to display received data on the display screen of the provider server computing device 112.

FIGS. 9-18 illustrate example user interface displays of the provider service 120. FIGS. 9-14, and 18 illustrate example user interface of the provider service 120 as displayed on a patient computing device 102.

Figure 9:
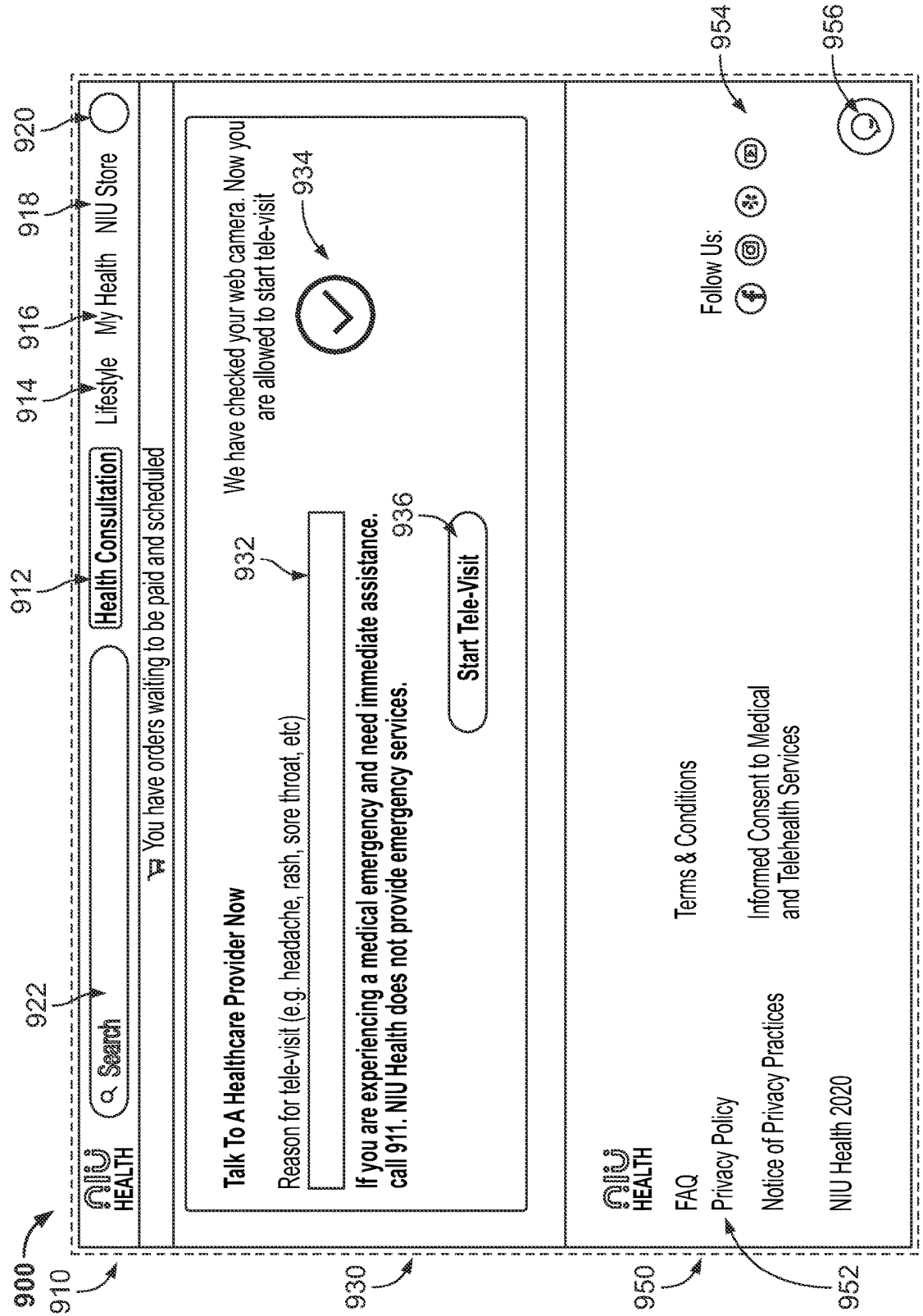
FIG. 9 illustrates an example user interface of the provider service of the health care provider system of FIG. 1, as displayed on a patient computing device.

FIG. 9 illustrates an example user interface 900 of the provider service 120 as displayed on a patient computing device 102. The example user interface 900 illustrates operation 602 of FIG. 6 and displays of a telehealth consultation request. The example user interface 900 includes a top banner 910, a main display area 930 and a bottom banner 950.

In some examples, the top banner 910 includes one or more options that allow the patient to navigate to different user interface display screens that enables different features associated with the provider service 120. For example, the top banner 910 includes a health consultation option 912, a lifestyle option 914, a "my health" option 916, a marketplace option 918, a patient profile option 920 and a search option 922.

For example, selecting the health consultation option 912 presents the user with one or more user interface displays that facilitate the telehealth consultation. In the current example from FIG. 9, the health consultation option 912 is highlighted to indicate that the option is currently selected by the patient and the display for requesting a telehealth consultation is presented on the patient computing device 102.

In some examples, selecting the lifestyle option 914 presents the patient with one or more user interface displays that allow the patient to access the communities 152 feature as described in relation to FIG. 4. The user interface display associated with selecting the lifestyle option 914 is further described in relation to FIG. 18.

In some examples, selecting the "my health" option 916 presents the patient with one or more user interface displays that allow the patent to access the patient's electronic medical records, including the user's health history, lab results, medication history, allergy information etc.

In some examples, selecting the marketplace option 918 presents the patient with one or more user interface displays that allow the patient to access the marketplace 154 feature as described in relation to FIG. 4. The marketplace user interface display may present the patient with one or more health, wellness and/or lifestyle related products that the patient may purchase.

In some examples, selecting the patient profile option 920 presents the patient with one or more user interface displays that allow the patient to access aspects of the patient's account/profile information as described in relation to FIG. 5. For example, the patient profile option 920 may include the features related to the authentication sub-module 162, the background information sub-module 164 and payment sub-module 168 of the member profile module 160 as described in relation to FIG. 5. The patient may select the patient profile option 920 to access and/or edit the account, profile and payment related information associated with the patient.

In some examples, the main display area 930 includes a "reason for visit" user input option 932 for the patient to enter the reason for the telehealth consultation. The main display area 930 also includes a display section 934 that lists if the patient computing device 102 is ready for the telehealth consultation. For example, if the patient computing device 102 does not have the camera or microphone enabled, then a display section 934 may include a message asking the patient to ensure that the camera and microphone are enabled. The main display area 930 may further include a selectable "start tele-visit" option 936 that initiates the telehealth consultation. In some examples, the selectable "start tele-visit" option 936 is enabled for selection upon the patient filling in the "reason for visit" user input option 932 and the display section 934 displays a message verifying that the patient computing device 102 is ready for the telehealth consultation.

In some examples, the bottom banner 950 can include one or more selectable options 952 related to the telehealth care provider. Selecting the one or more selectable options 952 may allow the patient to navigate to a user interface display screen including a display of frequently asked questions, privacy policy associated with the health care provider, a notice of privacy practices, terms & conditions and informed consent to medical and telehealth services. Selectable options associated with other types of information associated with the telehealth care provider may also be included within the bottom banner 950.

In other examples, the bottom banner 950 can also include one or more selectable links 954 that navigate the patient to one or more social media webpages/applications associated with the telehealth care provider, including Facebook, Instagram, Yelp, Twitter, YouTube, etc. In yet other examples, the bottom banner 950 can include a selectable "chat" options 956 for the patient to contact a customer service representative regarding any issues experienced by the patient.

In some examples, the options associated with the top banner 910 and the bottom banner 950 may remain the same the patient navigates through display screens by selecting one or more selectable options, whereas the main display area 930 may be altered to display data associated with the selected options.

Figure 10:
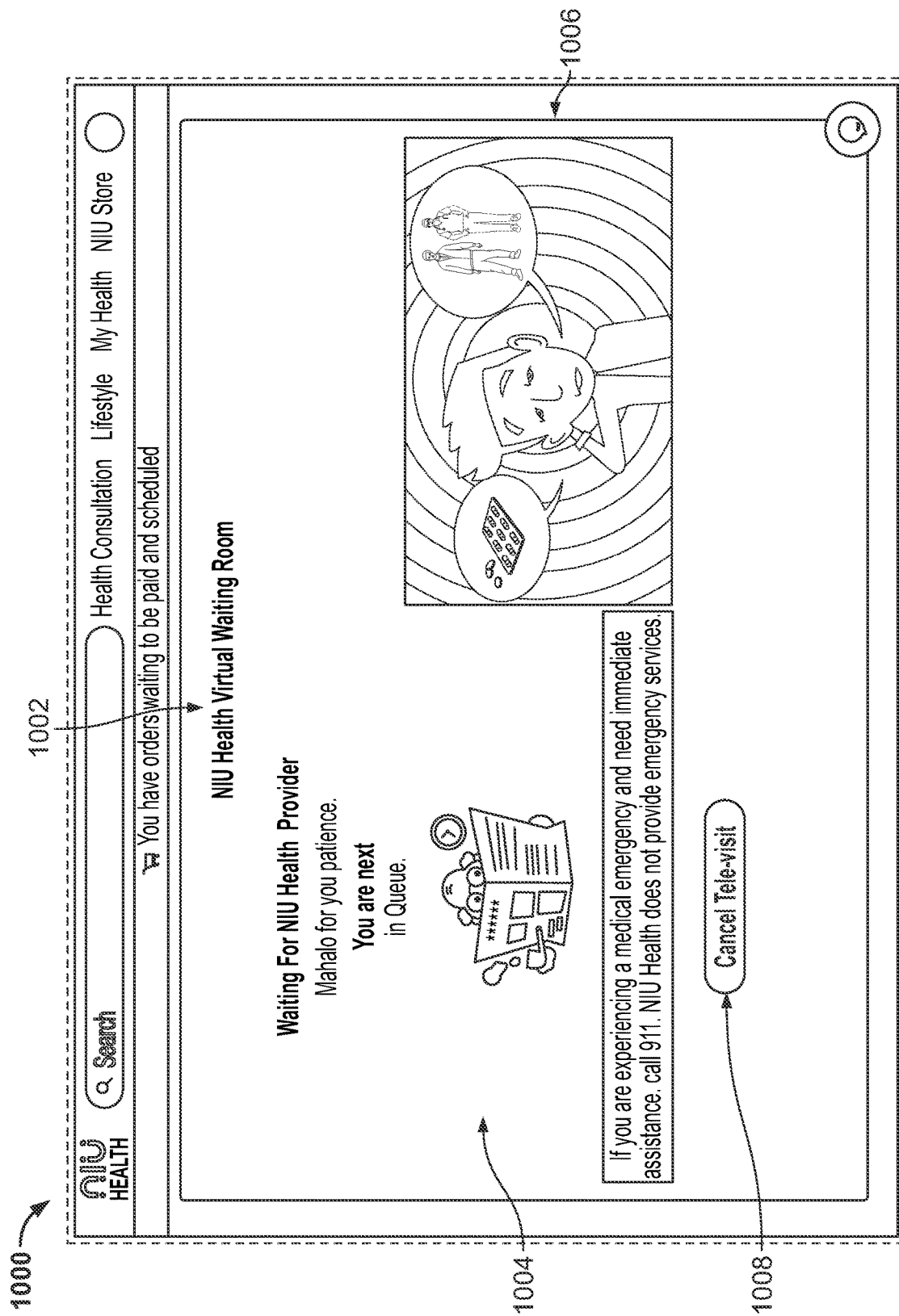
FIG. 10 illustrates another example user interface of the provider service of the health care provider system of FIG. 1, as displayed on the patient computing device.

FIG. 10 illustrates another example user interface 1000 of the provider service 120 as displayed on a patient computing device 102. The example user interface 1000 illustrates the virtual waiting room display 1002 as generated by the virtual waiting room 134. The virtual waiting room display 1002 includes a telehealth waiting room display area 1004 and a media content presentation display area 1006. The telehealth waiting room display area displays information related to the telehealth visit, including wait times, care provider's name, position within a virtual queue, etc.

In some examples, the media content presentation display area 1006 can include an embedded media player that enables the playback of the media content presentation described in relation to FIG. 2.

In some examples, the virtual waiting room display 1002 can also include a selectable "cancel tele-visit" option 1008 to cancel the initiated telehealth consultation and return the patient to the main menu.

Figure 11:
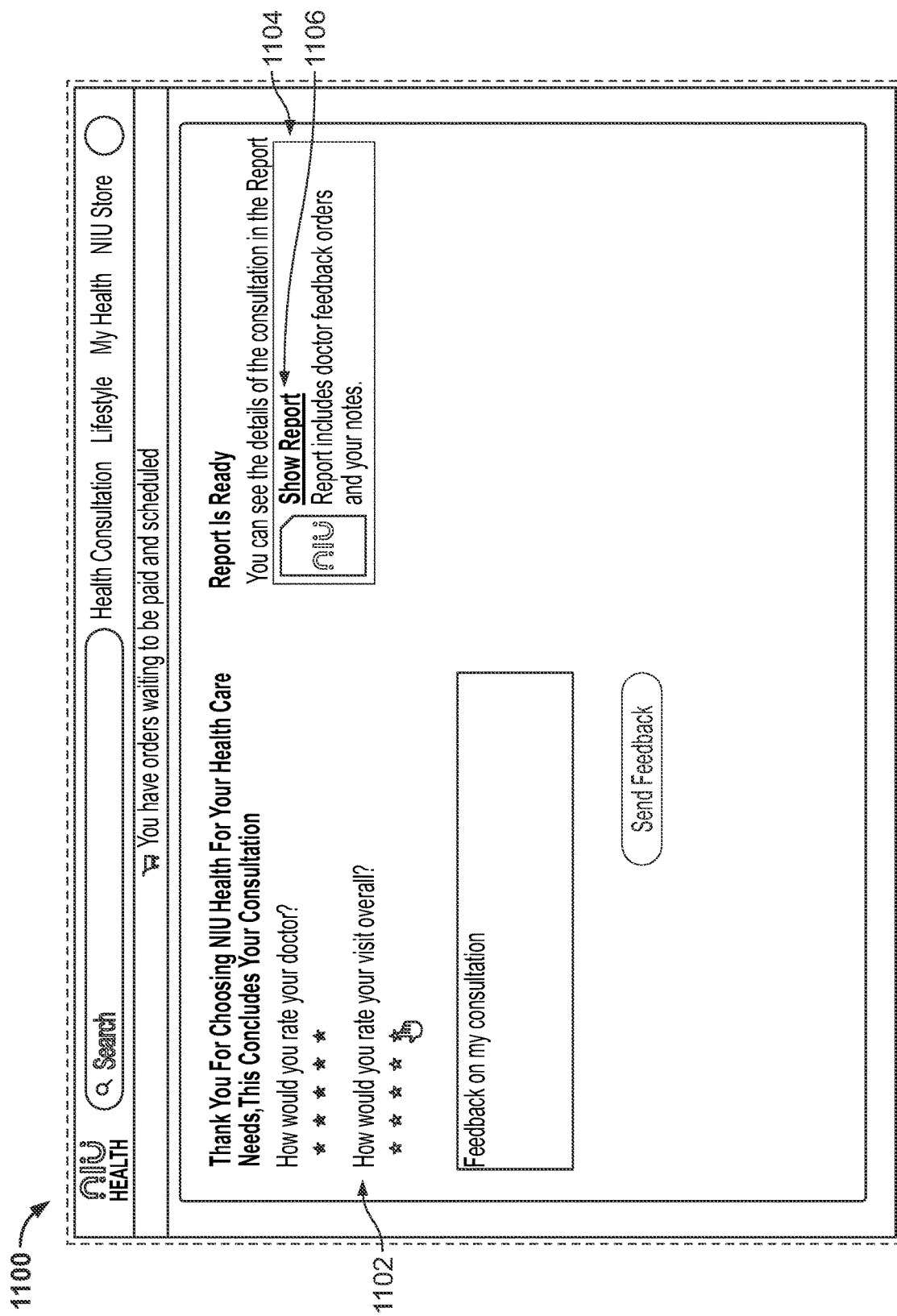
FIG. 11 illustrates another example user interface of the provider service of the health care provider system of FIG. 1, as displayed on the patient computing device.

FIG. 11 illustrates another example user interface 1100 of the provider service 120 as displayed on a patient computing device 102. The example user interface 1100 illustrates an "end of telehealth consultation" display 1102 that signals the completion of the telehealth consultation. The "end of telehealth consultation" display 1102 includes a feedback display area 1104 where the patient can input feedback related to the telehealth care provider, the telehealth care service, etc.

In some examples, the "end of telehealth consultation" display 1102 also illustrates a report display area 1106 that includes a "show report" link 1108. Selecting the "show report" link opens an example user interface 1200 described in further detail in relation to FIG. 12.

Figure 12:
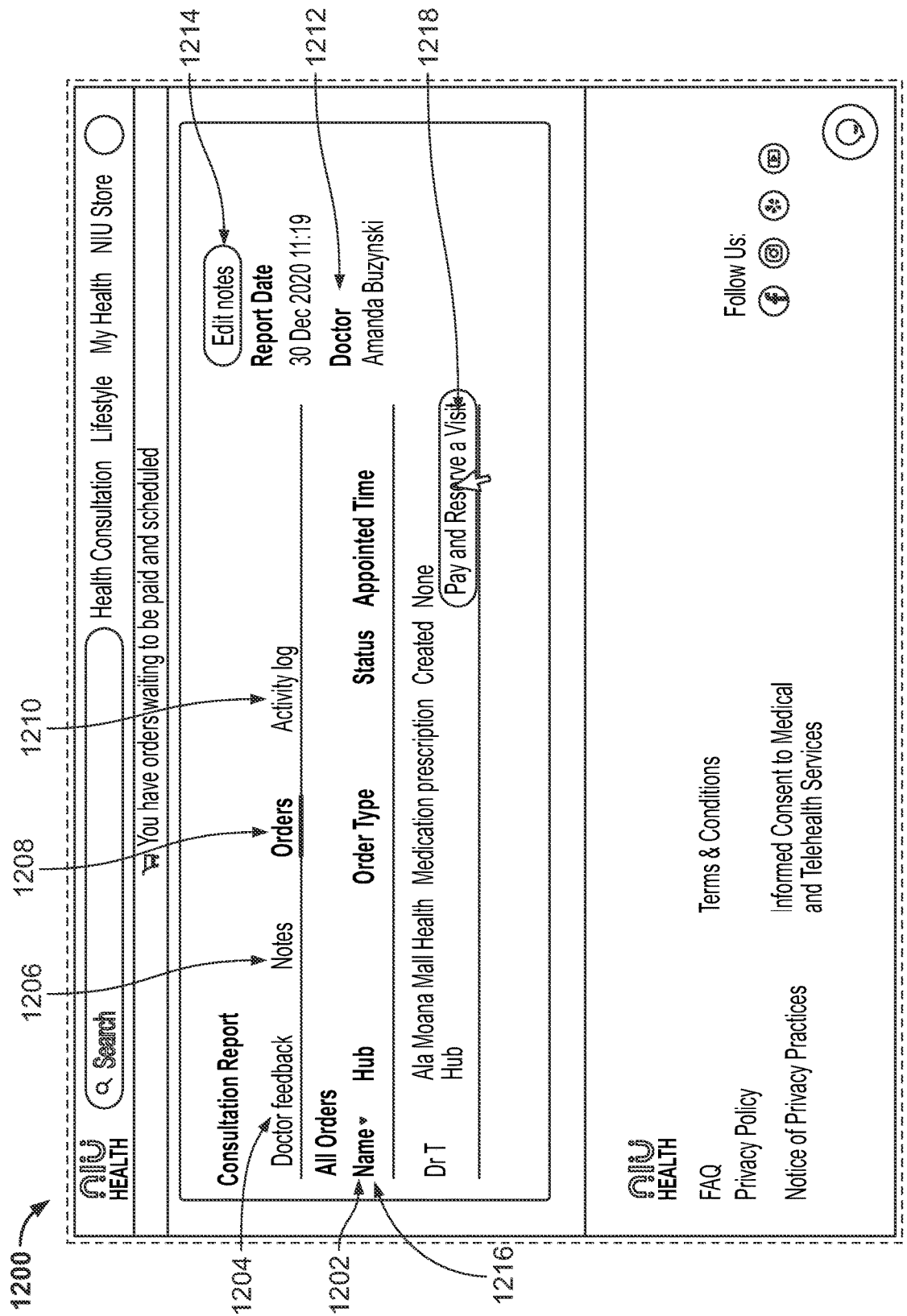
FIG. 12 illustrates another example user interface of the provider service of the health care provider system of FIG. 1, as displayed on the patient computing device.

FIG. 12 illustrates another example user interface 1200 of the provider service 120 as displayed on a patient computing device 102. The example user interface 1200 illustrates the "consultation report" display 1202. The "consultation report" display 1202 is configured to display one or more reports, orders, notes, feedback etc. associated with the recently completed telehealth consultation.

In some examples, the "consultation report" display 1202 includes one or more selectable options 1204-1210, wherein selecting the selectable options 1204-1210 displays additional data associated with the recently completed telehealth consultation.

For example, selecting the "doctor feedback" option 1204 may allow the patient to input specific feedback regarding the telehealth care provider. Selecting the "notes" option 1206 may allow the patient to view the notes entered by the telehealth care provider regarding the recently completed telehealth consultation. The "orders" option 1208 may allow the patient to view one or more orders entered by the telehealth care provider in association with the recently completed telehealth consultation. In some example, the orders may include orders for follow up in-person consultations, lab testing and/or prescription medication pickup. Selecting the "activity log" option 1210 may allow the patient to view a log of the activities associated with the recently completed telehealth consultation.

In some examples, the "consultation report" display 1202 may also include an additional notes display area 1212 that lists information associated with the consultation reports, such as the date when the report was saved, the name of the telehealth care provider that created/edited the consultation reports etc. The additional notes display area 1212 may also include a selectable "edit notes" option 1214 that can be selected by the patient to add patient notes or edit already created patient notes regarding the recently completed telehealth consultation.

In the current example from FIG. 12, the "orders" option 1208 of the "consultation report" display 1202 has been selected. As a result, the "consultation report" display 1202 includes an "all orders" display area that includes the name, the hub, the order type, the status and appointed time associated with the order. In the current example, order type is a medication prescription that has been created by "Dr. T." The prescription is to be picked up at the "Ala Moana Mall Health Hub" at the appointed time as selected by the patient using the "pay and reserve a visit" selectable option 1218. In some examples, the hub location and appointed time may be changed by the patient by selecting the "pay and reserve a visit" selectable option 1218. Selecting the "pay and reserve a visit" selectable option 1218 may cause the provider service 120 to display a date/time reservation window 1302 as described in relation to FIG. 13.

Figure 13:
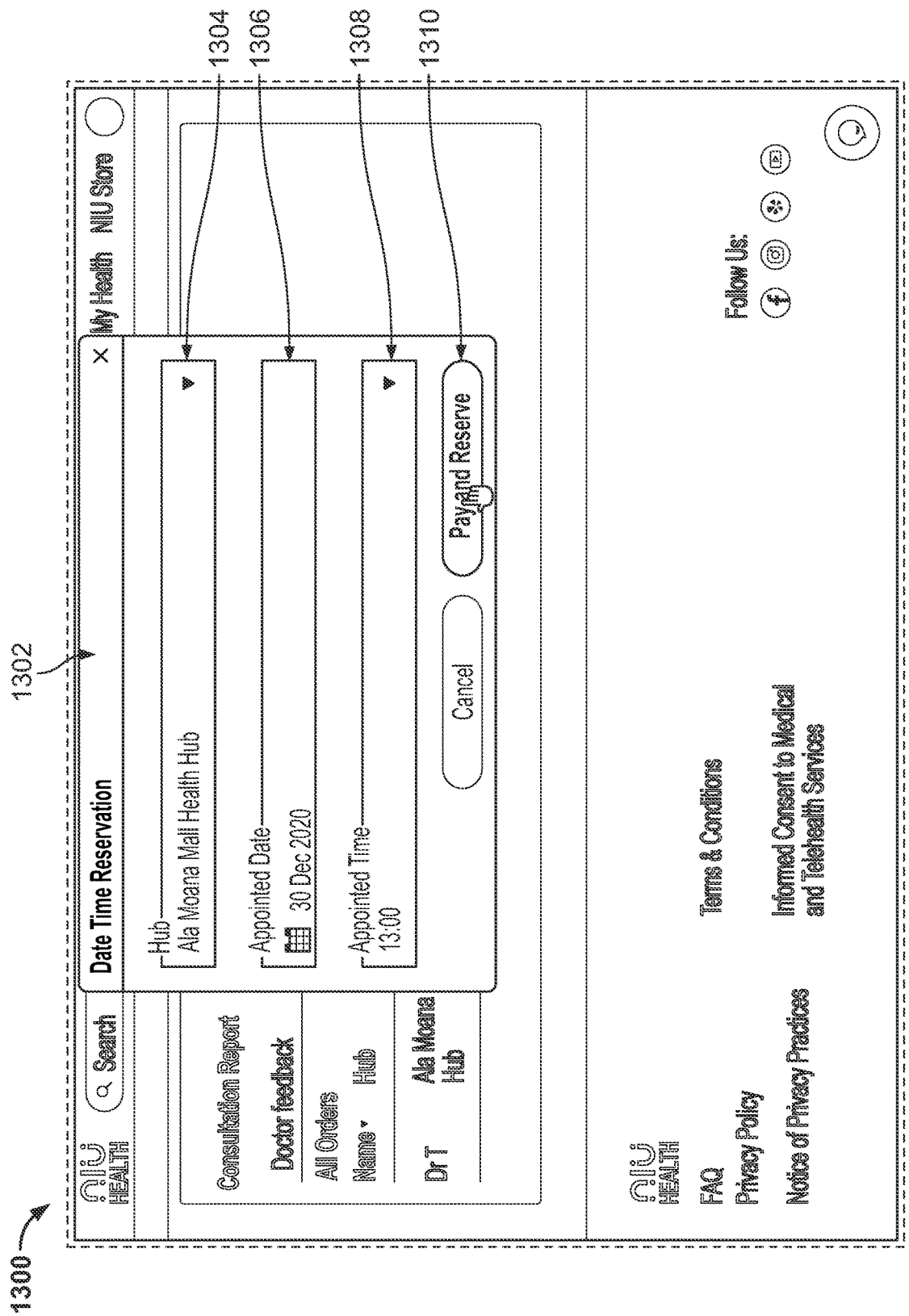
FIG. 13 illustrates another example user interface of the provider service of the health care provider system of FIG. 1, as displayed on the patient computing device.

FIG. 13 illustrates another example user interface 1300 of the provider service 120 as displayed on a patient computing device 102. The example user interface 1300 illustrates a date/time reservation window 1302 that may be opened as a result of the patient selecting the "pay and reserve a visit" selectable option 1218 on the example user interface 1200 as described in relation to FIG. 12.

In some examples, the date/time reservation window 1302 can include a "hub" selectable option 1304, an "appointment date" selectable option 1306 and an "appointment time" selectable option 1308. The "hub" selectable option 1304 may allow the patient to select a hub care facility location that is convenient for the patient. The "appointment date" selectable option 1306 may allow the patient to select the date of the appointment to pick up the medication from a medication dispenser 188 associated with the selected hub care facility. The "appointment time" selectable option 1308 may allow the patient to select the time of the appointment to pick up the medication from the medication dispenser 188 associated with the selected hub care facility.

Figure 14:
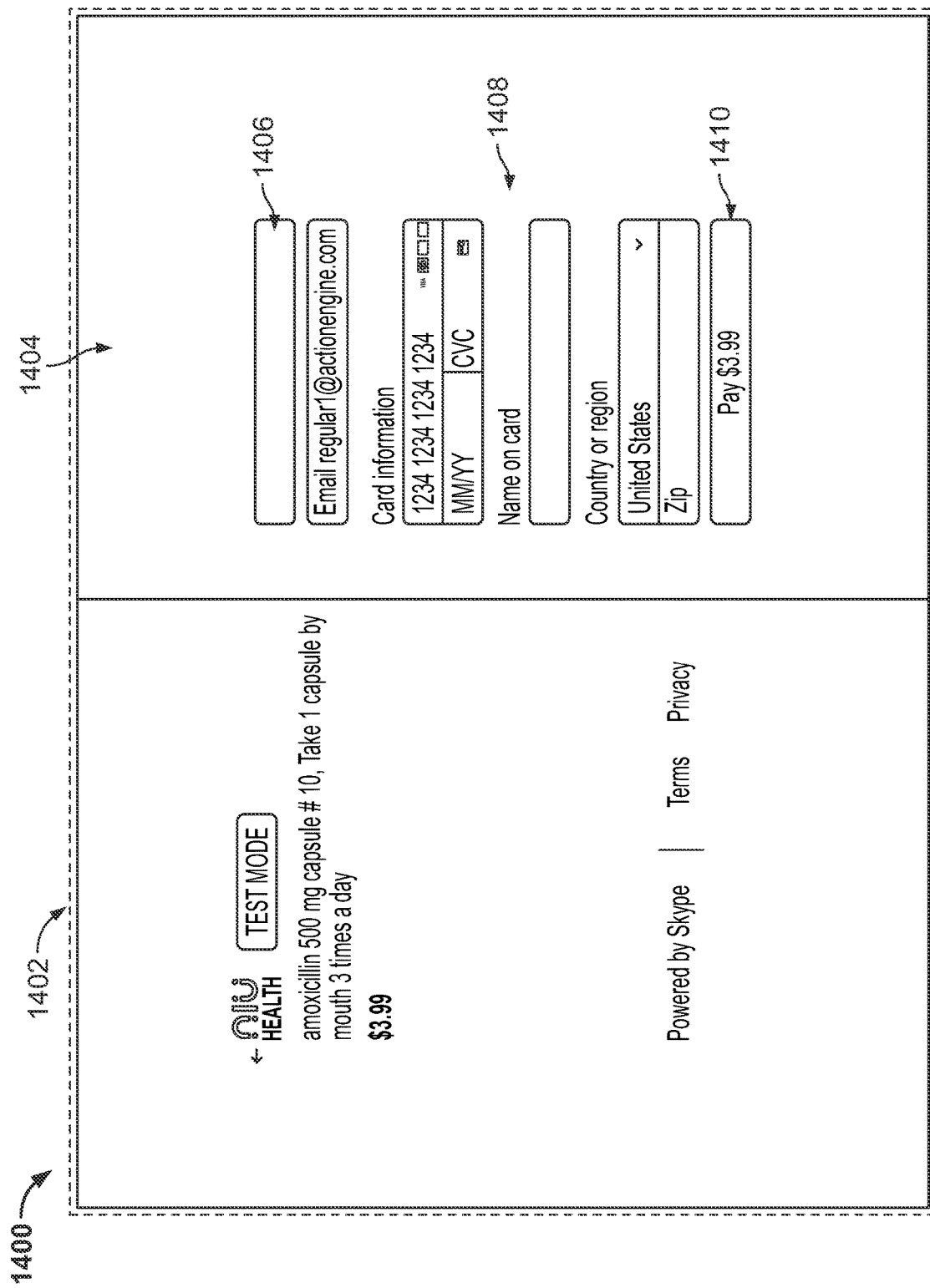
FIG. 14 illustrates another example user interface of the provider service of the health care provider system of FIG. 1, as displayed on the patient computing device.

Further, the date/time reservation window 1302 can also include a "pay and reserve" selectable option 1310 that navigates the user interface 1300 to a payment user interface 1400 that is described in greater detail in relation to FIG. 14.

FIG. 14 illustrates another example payment user interface 1400 of the provider service 120 as displayed on a patient computing device 102. The example payment user interface 1400 illustrates is configured to enable the patient to enter payment information. The example payment user interface 1400 includes an order summary display area 1402 and a payment information summary display area 1404.

In some examples, the order summary display area 1402 displays details regarding the entered order, including medication name, dosage, instructions and cost information. In some other examples, the payment information summary display area 1404 includes a plurality patient information input options, including an patient email address input 1406 for the patient to enter the patient's email address and a patient payment information input 1408 for the patient to enter payment information such as credit/debit card number, expiration date, name on the card, billing address etc.

In some examples, the payment user interface 1400 includes a selectable "pay" option 1410. Selecting the selectable "pay" option 1410 allows the patient to authorize the payment for the order.

Figure 15:
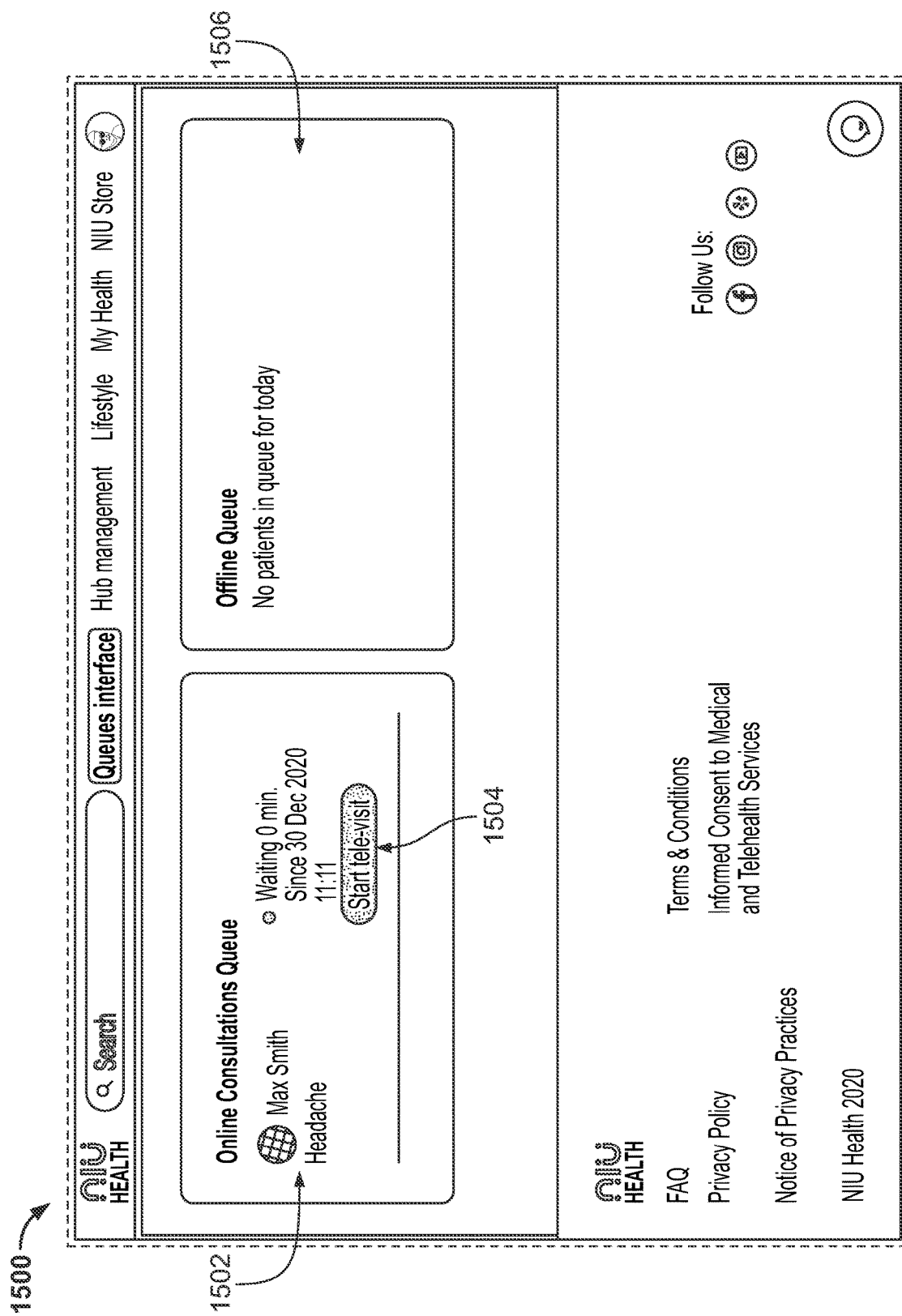
FIG. 15 illustrates an example user interface of the provider service of the health care provider system of FIG. 1, as displayed on a telehealth care provider computing device.
Figure 16:
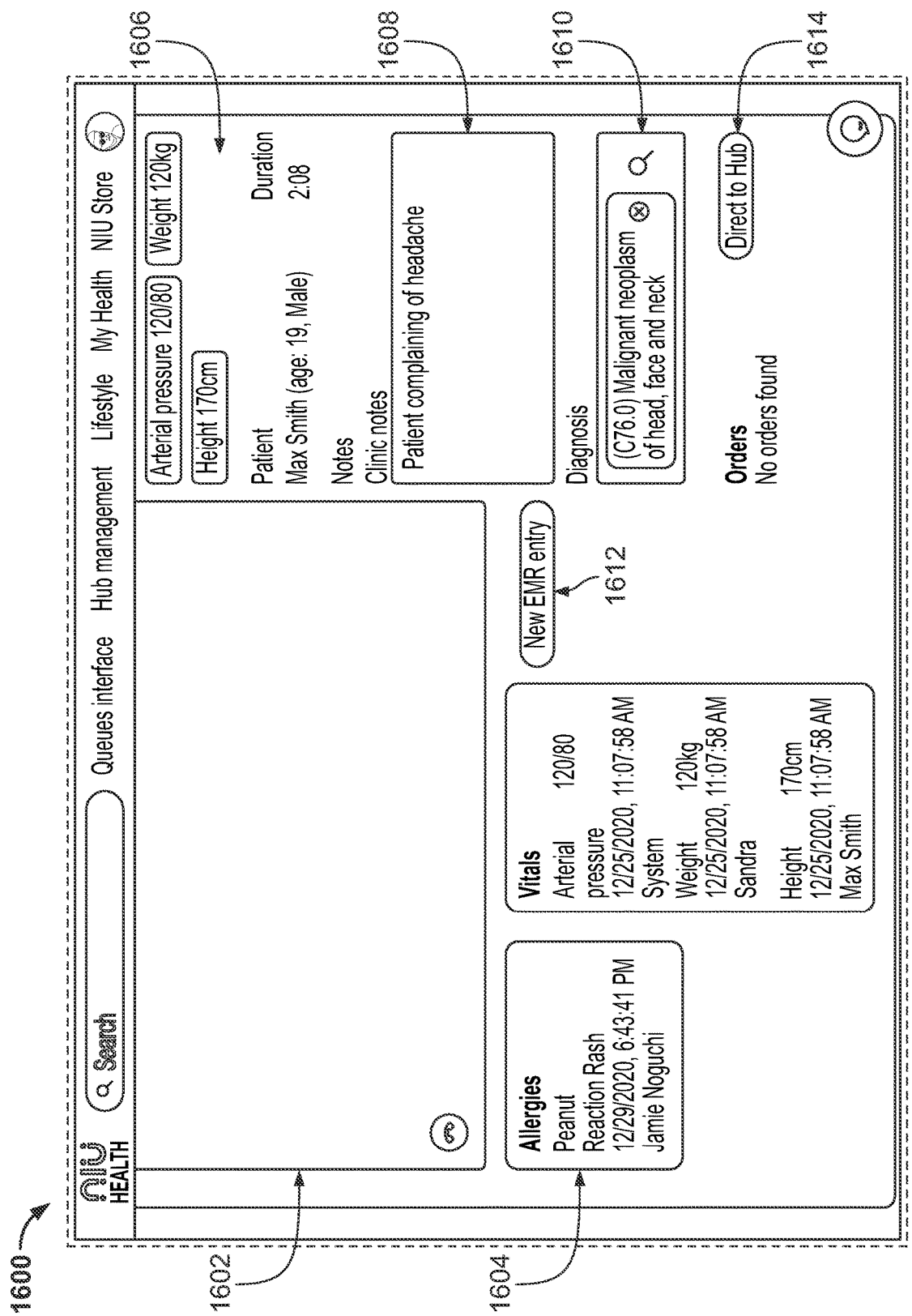
FIG. 16 illustrates another example user interface of the provider service of the health care provider system of FIG. 1, as displayed on the telehealth care provider computing device.
Figure 17:
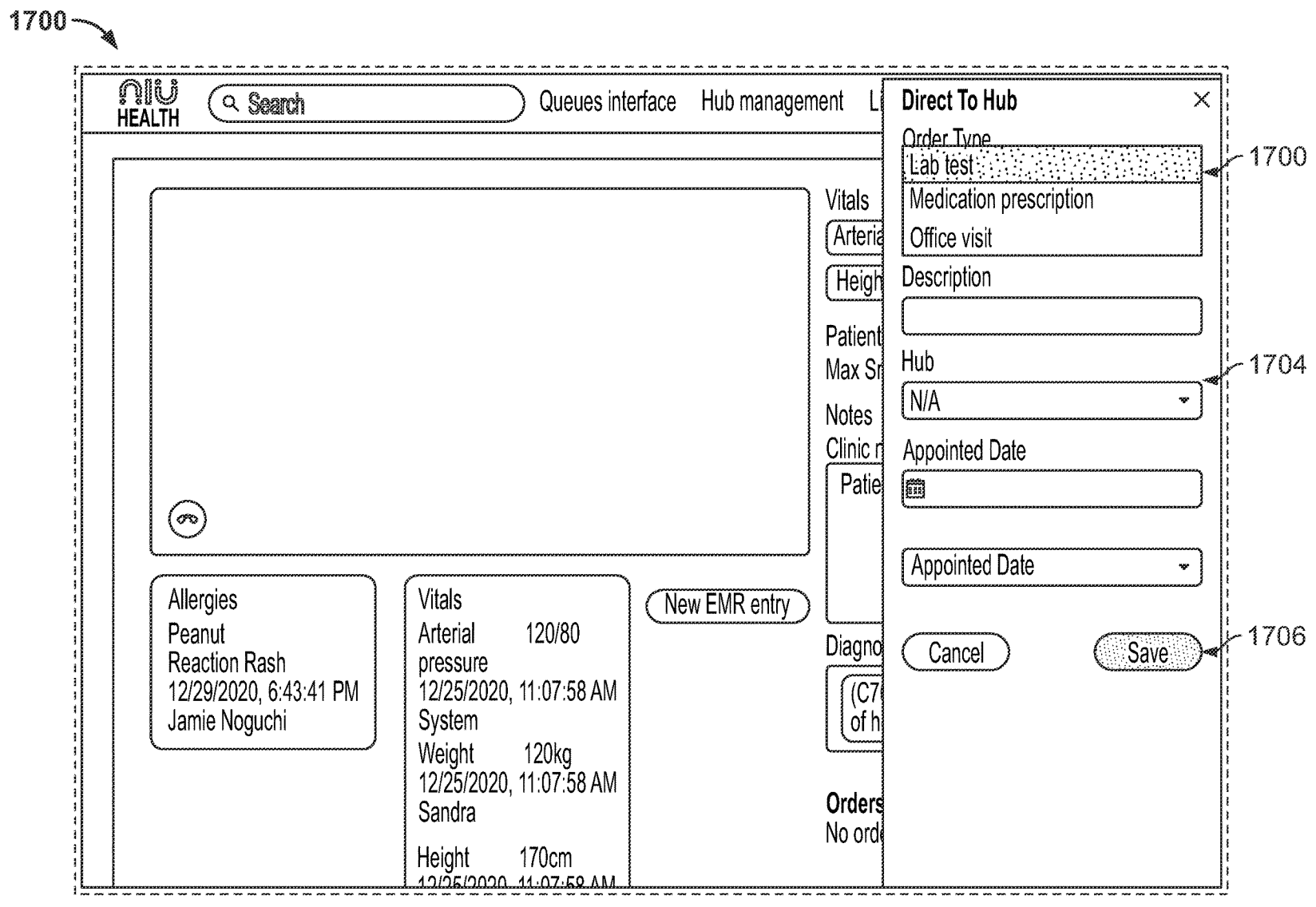

FIGS. 15-17 illustrate example user interface of the provider service 120 as displayed on a telehealth care provider computing device 110.

FIG. 15 illustrates an example user interface 1500 of the provider service 120 as displayed on a telehealth care provider computing device 110. The example user interface 1500 corresponds to what is displayed on the telehealth care provider computing device 110 after the patient has completed the playback of the media content presentation and is waiting to meet with the telehealth care provider.

In some examples, the user interface 1500 can include an online consultations queue display area 1502 and an offline consultations queue display area 1506. For example, the online consultations queue display area 1502 includes information related to patients that are currently online and waiting in a virtual queue for a consultation with the telehealth care provider.

In some examples, the online consultations queue display area 1502 can display queue information as a list of patient names, a brief description of the symptoms, and the amount of time the patient has been waiting for the consultation. When available, the telehealth care provider may be able to start the telehealth consultation with a particular patient by selecting a selectable "start tele-visit" option 1504 adjacent to the listing of the patient on the online consultations queue display area 1502.

In some examples, in addition to the waiting time, the user interface 1500 may also include a display of whether the patient is still in the process of viewing the media content presentation or if the patient has completed the media content presentation. The telehealth care provider may have the option to interrupt the lockout mode that is initiated by the virtual waiting room 134 on the patient computing device 102 during the media content presentation by selecting the "start tele-visit" option 1504 while the user interface 1500 still displays that the patient has not concluded the media content presentation. In some examples, there may be a selectable option on the user interface 1500. In other examples, the telehealth care provider selecting the "start tele-visit" option 1504 may automatically trigger the interruption.

For example, selecting the "start tele-visit" option 1504 may automatically conclude the lockout mode initiated by the virtual waiting room 134 on the patient computing device 102, conclude the media content presentation and start the telehealth consultation. In other examples, if the media content presentation has not concluded and the virtual waiting room 134 is still under the lockout mode, selecting the "start tele-visit" option 1504 may trigger a secondary message to be displayed on the user interface 1504. The secondary message may ask the telehealth care provider to confirm that they would like to interrupt the media content presentation.

In other examples, the offline consultations queue display area 1506 can display queue information as a list of patient names similar to the online consultations queue display area 1502. However, the offline consultations queue display area 1506 lists patients that have previously scheduled a telehealth consultation at a future time with the telehealth care provider but are currently not online to begin consultations.

FIG. 16 illustrates an example user interface 1600 of the provider service 120 as displayed on a telehealth care provider computing device 110. The example user interface 1600 illustrates the virtual exam room interface generated by the virtual exam room 138 as seen by the telehealth care provider on the telehealth care provider computing device 110.

In some examples, the user interface 1600 includes a video display area 1602 that displays a live audio/visual stream of the patient as captured by a camera and microphone associated with the patient computing device 102. The live video of the patient may assist the telehealth care provider in diagnosing the patient's health condition more efficiently.

In some examples, the user interface 1600 can also include a previous patient data display area 1604 that displays health information related to the patient from the health records associated with the patient, including allergy information, vitals, etc. In other examples, the user interface 1600 can also include a current patient data display area 1606 that displays current health information related to the patient, including allergy information, vitals, current medications, etc.

In some examples the user interface 1600 can also include a "notes" section 1608 where the telehealth care provider can take notes throughout the telehealth consultation. Once the telehealth care provider has determined the patient's diagnosis, the telehealth care provider may be able to select the diagnosis from the selectable diagnosis option 1610 on example user interface 1600. Additionally, the telehealth care provider may also be able to create a new electronic medical record entry by selecting the "new EMR entry" option 1612 on the example user interface 1600.

In some examples, based on the diagnosis and the overall consultation, the telehealth care provider may need to direct the patient to a hub care facility for a plurality of reasons including—to complete a follow up in-person consultation with a care provider, to complete lab work such as blood draws or x-rays, and/or to pick up medication prescribed by the telehealth care provider during the telehealth consultation. The selectable "direct to hub" option 1614 enables the telehealth care provider to enter additional information regarding the reason for directing the patient to a hub care facility and create an appointment date/time and location. The example "direct to hub" user interface 1700 is described in further detail in relation to FIGS. 17 and 18.

FIG. 17 illustrates an example "direct to hub" user interface 1700 of the provider service 120 as displayed on a telehealth care provider computing device 110. The example "direct to hub" user interface 1700 opens as a new window or overlays the example user interface 1600 as a result of the telehealth care provider selecting the selectable "direct to hub" option 1614 as described in FIG. 16.

In some examples, the "direct to hub" user interface 1700 includes one or more selectable options including "order type" option 1702 and one or more additional options 1704 that is customized based on the selected "order type" option 1702. For example, the selectable "order type" option 1702 includes a plurality of options including: "lab test," "medication prescription" and "office visit." Depending on the "order type" that is selected, the one or more additional options 1704 may automatically change. For example, selecting "lab test" for the "order type" may result in additional options 1704 such as description, hub location, appointed date and appointed time. However, selecting "medication prescription" for the "order type" may result in additional options 1704 such as name of telehealth care provider, prescribed medication, instructions and hub location.

In some examples, when the telehealth care provider completes the selectable options 1702, 1704 and selects the "save" option 1706, the user virtual exam room user interface display on the patient computing device 102 may automatically be updated to the "end of telehealth consultation" display 1102 and the "report" display area 1106 of the example user interface 1100 on the patient computing device 102 may automatically be updated to include a link to the report.

Figure 18:
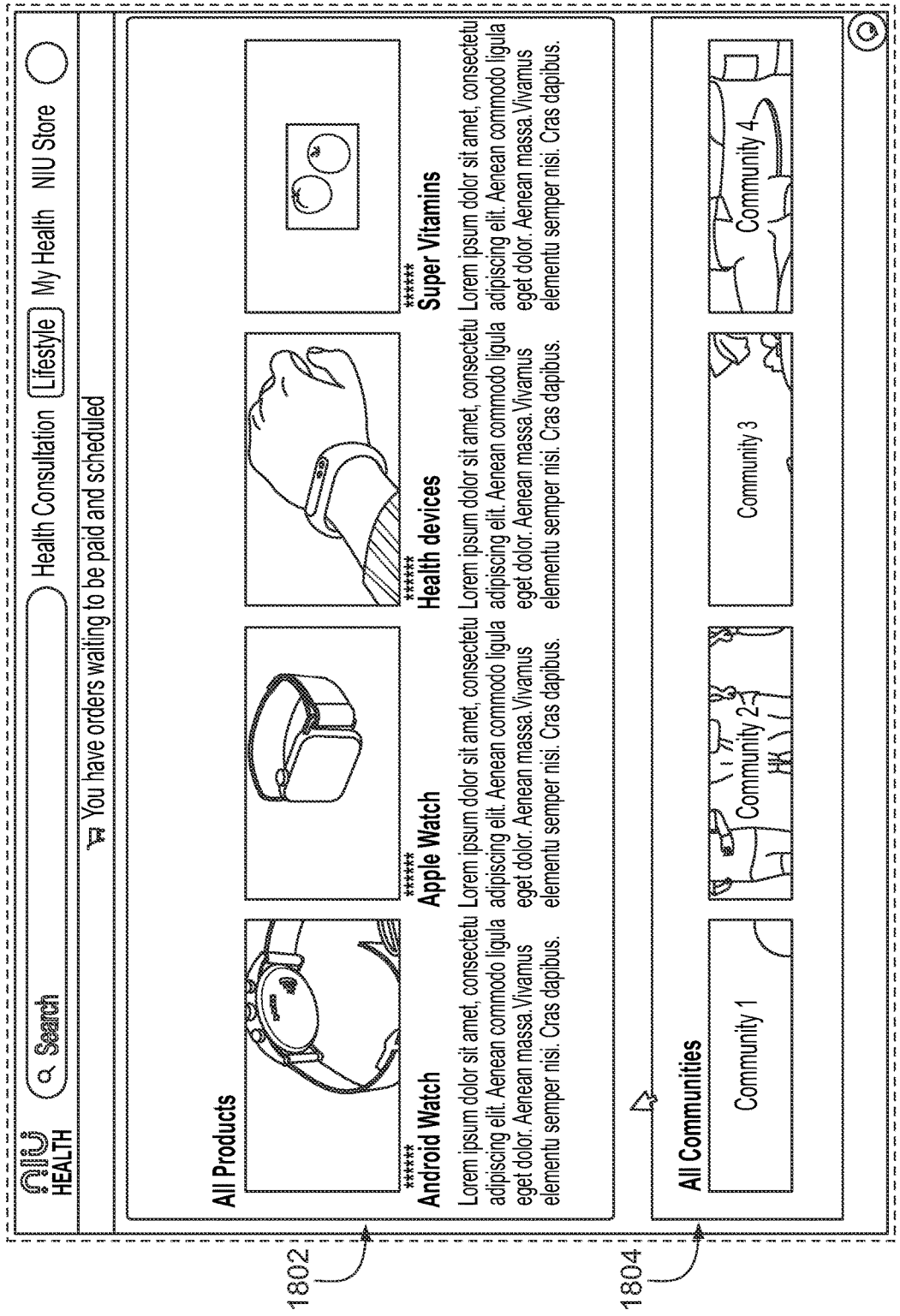
FIG. 18 illustrates another example user interface of the provider service of the health care provider system of FIG. 1, as displayed on the patient computing device.

FIG. 18 illustrates another example user interface 1800 of the provider service 120 as displayed on a patient computing device 102. The example user interface 1800 illustrates the communities 152 feature of the social hub module 150 as described in FIG. 4. In some examples, selecting the lifestyle option 914 presents the user with one or more user interface displays that allow the patient to access the communities 152 feature.

For example, the user interface 1800 includes a plurality of sections 1802, 1804 that include one or more selectable sub-sections with articles, products, communities, etc. related to the particular section. For example, in the current example from FIG. 18, section 1802 relates to products related to health, wellness and/or lifestyle. Each of the sub-sections under the section 1802 includes a health, wellness or lifestyle product. Further, in the current example from FIG. 18, section 1804 relates to communities related to health, wellness and/or lifestyle. Each of the sub-sections included within section 1804 includes a community related to a specific category or topic.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A method of facilitating a healthcare appointment at a care facility, wherein the method comprises:
    using one or more computing devices:

providing access to a virtual exam room including a provider portal and a patient portal;
facilitating a telehealth consultation between a patient and a care provider via the virtual exam room;
receiving, from the care provider, an indication that the patient has a need to visit the care facility;
scheduling the healthcare appointment for the patient at the care facility for an available date and time via the virtual exam room;
sending the date and the time to the patient via the patient portal;
sending a first unlock code for the care facility for the patient, wherein the first unlock code is required to unlock a door to the care facility for the healthcare appointment;
receiving, from an entryway control system associated with the care facility, a second unlock code;
determining that the second unlock code matches the first unlock code; and
upon determining that the second unlock code matches the first unlock code, causing the entryway control system to unlock the door to the care facility.

2. The method of claim 1, wherein determining that the second unlock code matches the first unlock code further includes:
determining that the second unlock code was received at the entryway control system on the date and within a predetermined time interval surrounding the time.

3. The method of claim 1, wherein the first unlock code is a Quick Response (QR) code.

4. The method of claim 3, wherein the entry way control system includes a QR scanner.

5. The method of claim 1, wherein the care facility includes a medication locker.

6. The method of claim 5, wherein the medication locker includes a medication locker scanner that controls access to the medication locker.

7. The method of claim 6, further comprising:
sending a first medication locker unlock code to the patient during or following the healthcare appointment;
receiving, from the medication locker scanner, a second medication locker unlock code;
determining that the second medication locker unlock code matches the first medication locker unlock code; and
upon determining that the second medication locker unlock code matches the first medication locker unlock code, causing the medication locker scanner to unlock the medication locker.

8. The method of claim 7, further comprising:
sending a medication pickup date and a medication pickup time.

9. The method of claim 8, wherein determining that the second medication locker unlock code matches the first medication locker unlock code further comprises:
determining that the second medication locker unlock code was received at the medication locker scanner on the medication pickup date and within a predetermined time interval surrounding the medication pickup time.

10. The method of claim 1, wherein the care facility is a building that houses one or more exam rooms.

11. A computing system for facilitating a healthcare appointment at a care facility, wherein the computing system comprises:
one or more processors; and
memory including instructions that when executed by the one or more processors, cause the computing system to:

provide access to a virtual exam room including a provider portal and a patient portal;
facilitate a telehealth consultation between a patient and a care provider via the virtual exam room;
receive a request to schedule the healthcare appointment for a patient from a patient device via the patient portal;
automatically schedule the healthcare appointment for the patient at the care facility for an available date and time via the virtual exam room;
automatically send a confirmation of the healthcare appointment including the date and the time to the patient via the patient portal;
automatically send a first unlock code for the care facility for the patient, wherein the first unlock code is required to unlock a door to the care facility;
receive, from an entryway control system associated with the care facility, a second unlock code;
determine that the second unlock code matches the first unlock code; and
upon determining that the second unlock code matches the first unlock code, cause the entryway control system to unlock the door to the care facility.

12. The system of claim 11, wherein determining that the second unlock code matches the first unlock code further includes:
determining that the second unlock code was received at the entryway control system on the date and within a predetermined time interval surrounding the time.

13. The system of claim 11, wherein the first unlock code is a Quick Response (QR) code.

14. The system of claim 13, wherein the entry way control system includes a QR scanner.

15. The system of claim 11, wherein the care facility includes a medication locker.

16. The system of claim 15, wherein the medication locker includes a medication locker scanner that controls access to the medication locker.

17. The system of claim 16, wherein the instructions when executed by the one or more processors, further cause the computing system to:
send a first medication locker unlock code to the patient during or following the healthcare appointment;
receive, from the medication locker scanner, a second medication locker unlock code;
determine that the second medication locker unlock code matches the first medication locker unlock code; and
upon determining that the second medication locker unlock code matches the first medication locker unlock code, cause the medication locker scanner to unlock the medication locker.

18. The system of claim 17, wherein the instructions when executed by the one or more processors, further cause the computing system to:
send a medication pickup date and a medication pickup time.

19. The system of claim 18, wherein determining that the second medication locker unlock code matches the first medication locker unlock code further comprises:
determining that the second medication locker unlock code was received at the medication locker scanner on the medication pickup date and within a predetermined medication pickup time interval surrounding the medication pickup time.

20. A method of facilitating a healthcare appointment at a care facility, wherein the method comprises:

providing access to a virtual exam room including a provider portal and a patient portal;

facilitating a telehealth consultation between a patient and a care provider via the virtual exam room;

sending a request from a patient device for the healthcare appointment at the care facility for an available date and time via the patient portal;

receiving at the patient device a confirmation for the healthcare appointment at the care facility for the date and the time via the patient portal;

receiving an unlock code for the care facility at the patient device, wherein the unlock code is required to unlock a door to the care facility;

providing, to the patient device, the unlock code at an entryway control system associated with the care facility on the date and within a predetermined time interval surrounding the time; and upon providing the unlock code at the entryway control system on the date and within a predetermined time interval surrounding the time, being granted access to the care facility via the door to the care facility.

* * * * *